(12) United States Patent  
Vallapureddy et al.

(10) Patent No.: US 8,521,299 B2  
(45) Date of Patent: Aug. 27, 2013

(54) REMOTE MONITORING AND CONTROL OF IMPLANTABLE DEVICES

(75) Inventors: Vineel Vallapureddy, Coon Rapids, MN (US); Adrianus P. Donders, Andover, MN (US); Satish Ramadhyani, Minneapolis, MN (US); Wu Wang, Lakeville, MN (US); Hang Chan, Chanhassen, MN (US)

(73) Assignee: EnteroMedics Inc., St. Paul, MN (US)

( * ) Notice: Subject to any disclaimer, the term of this patent is extended or adjusted under 35 U.S.C. 154(b) by 0 days.

(21) Appl. No.: 13/292,530

(22) Filed: Nov. 9, 2011

(65) Prior Publication Data

US 2012/0065706 A1 Mar. 15, 2012

Related U.S. Application Data

(63) Continuation of application No. 11/716,353, filed on Mar. 9, 2007, now Pat. No. 8,068,918.

(51) Int. Cl.
*A61N 1/372* (2006.01)

(52) U.S. Cl.
USPC ........ 607/59; 607/1; 607/2; 607/60; 607/115; 607/116; 128/920

(58) Field of Classification Search
USPC .............. 607/1–2, 59–60, 115–116; 128/920
See application file for complete search history.

(56) References Cited

U.S. PATENT DOCUMENTS

| | | |
|---|---|---|
| 3,727,616 A | 4/1973 | Lenzkes |
| 3,796,221 A | 3/1974 | Hagfors |
| 3,942,535 A | 3/1976 | Schulman |
| 4,082,097 A | 4/1978 | Mann et al. |
| 4,369,530 A | 1/1983 | Robinson et al. |
| 4,498,478 A | 2/1985 | Bourgeois |
| 4,577,633 A | 3/1986 | Berkovits et al. |
| 4,592,359 A | 6/1986 | Galbraith |
| 4,608,985 A | 9/1986 | Crish et al. |
| 4,612,934 A | 9/1986 | Borkan |
| 4,793,353 A | 12/1988 | Borkan |
| 4,846,180 A | 7/1989 | Buffet |
| 4,979,511 A | 12/1990 | Terry, Jr. |
| 5,215,089 A | 6/1993 | Baker, Jr. |
| 5,251,634 A | 10/1993 | Weinberg |

(Continued)

FOREIGN PATENT DOCUMENTS

| | | |
|---|---|---|
| EP | 1 666 087 A2 | 6/2006 |
| WO | WO 01/43821 A1 | 6/2001 |
| WO | 2012044472 A2 | 4/2012 |
| WO | 2012060874 A2 | 5/2012 |

OTHER PUBLICATIONS

Invitation to Pay Additional Fees with Partial International Search cited in PCT/US2008/055098 mailed Jul. 11, 2008.

(Continued)

*Primary Examiner* — Deborah Malamud
(74) *Attorney, Agent, or Firm* — Merchant & Gould P.C.

(57) ABSTRACT

A treatment system includes a regulator implanted within a patient, a computing device storing at least one patient database associated with the patient in whom the regulator is implanted, and a data transfer device. The data transfer device provides bi-directional communication (e.g., voice communication) and a data exchange (e.g., a treatment history, a patient database, and operational instructions) between the regulator and the computing device. A programmer can obtain patient reports and/or default treatment values from the computing device based on the data exchange.

13 Claims, 16 Drawing Sheets

(56) References Cited

U.S. PATENT DOCUMENTS

| | | |
|---|---|---|
| 5,263,480 A | 11/1993 | Wernicke et al. |
| 5,279,292 A | 1/1994 | Baumann et al. |
| 5,360,437 A | 11/1994 | Thompson |
| 5,391,188 A | 2/1995 | Nelson et al. |
| 5,531,778 A | 7/1996 | Maschino et al. |
| 5,591,217 A | 1/1997 | Barreras |
| 5,716,377 A | 2/1998 | Rise et al. |
| 5,733,313 A | 3/1998 | Barreras, Sr. et al. |
| 5,749,907 A | 5/1998 | Mann |
| 5,755,747 A | 5/1998 | Daly et al. |
| 5,836,989 A | 11/1998 | Shelton |
| 5,876,425 A | 3/1999 | Gord et al. |
| 5,928,272 A | 7/1999 | Adkins et al. |
| 6,045,513 A | 4/2000 | Stone et al. |
| 6,067,474 A | 5/2000 | Schulman et al. |
| 6,102,874 A | 8/2000 | Stone et al. |
| 6,167,311 A | 12/2000 | Rezai |
| 6,205,358 B1 | 3/2001 | Haeg et al. |
| 6,208,902 B1 | 3/2001 | Boveja |
| 6,243,606 B1 | 6/2001 | Mann et al. |
| 6,278,258 B1 | 8/2001 | Echarri et al. |
| 6,280,409 B1 | 8/2001 | Stone et al. |
| 6,285,908 B1 | 9/2001 | Mann et al. |
| 6,305,381 B1 | 10/2001 | Weijand et al. |
| 6,321,117 B1 | 11/2001 | Koshiol et al. |
| 6,356,786 B1 | 3/2002 | Rezai et al. |
| 6,363,282 B1 | 3/2002 | Nichols et al. |
| 6,366,814 B1 | 4/2002 | Boveja et al. |
| 6,381,496 B1 | 4/2002 | Meadows et al. |
| 6,418,346 B1 | 7/2002 | Nelson et al. |
| 6,438,423 B1 | 8/2002 | Rezai et al. |
| 6,473,652 B1 | 10/2002 | Sarwal et al. |
| 6,505,074 B2 | 1/2003 | Boveja et al. |
| 6,505,075 B1 | 1/2003 | Weiner |
| 6,505,077 B1 | 1/2003 | Kast et al. |
| 6,516,227 B1 | 2/2003 | Meadows et al. |
| 6,564,102 B1 | 5/2003 | Boveja |
| 6,587,719 B1 | 7/2003 | Barrett et al. |
| 6,600,956 B2 | 7/2003 | Maschino et al. |
| 6,609,025 B2 | 8/2003 | Barrett et al. |
| 6,611,715 B1 | 8/2003 | Boveja |
| 6,614,406 B2 | 9/2003 | Amundson et al. |
| 6,615,081 B1 | 9/2003 | Boveja |
| 6,662,052 B1 | 12/2003 | Sarwal et al. |
| 6,664,763 B2 | 12/2003 | Echarri et al. |
| 6,678,560 B1 | 1/2004 | Gilkerson et al. |
| 6,690,974 B2 | 2/2004 | Archer et al. |
| 6,760,626 B1 | 7/2004 | Boveja |
| 6,819,956 B2 | 11/2004 | DiLorenzo |
| 6,850,803 B1 | 2/2005 | Jimenez et al. |
| 6,879,859 B1 | 4/2005 | Boveja |
| 6,892,097 B2 | 5/2005 | Holsheimer |
| 6,895,280 B2 | 5/2005 | Meadows et al. |
| 6,907,295 B2 | 6/2005 | Gross et al. |
| 6,934,580 B1 | 8/2005 | Osorio et al. |
| 6,985,773 B2 | 1/2006 | Von Arx et al. |
| 7,003,353 B1 | 2/2006 | Parkhouse |
| 7,076,307 B2 | 7/2006 | Boveja et al. |
| 7,082,333 B1 | 7/2006 | Bauhahn et al. |
| 7,146,223 B1 | 12/2006 | King |
| 7,167,750 B2 | 1/2007 | Knudson et al. |
| 7,191,012 B2 | 3/2007 | Boveja et al. |
| 7,239,918 B2 | 7/2007 | Strother et al. |
| 7,283,867 B2 | 10/2007 | Strother et al. |
| 7,286,881 B2 | 10/2007 | Schommer et al. |
| 7,486,993 B2 | 2/2009 | Gilmer et al. |
| 7,551,960 B2 | 6/2009 | Forsberg et al. |
| 7,715,913 B1 | 5/2010 | Froman et al. |
| 7,725,195 B2 | 5/2010 | Lima et al. |
| 7,801,615 B2 | 9/2010 | Meadows et al. |
| 7,813,809 B2 | 10/2010 | Strother et al. |
| 8,239,027 B2 | 8/2012 | Imran |
| 8,260,426 B2 | 9/2012 | Armstrong et al. |
| 2001/0051787 A1 | 12/2001 | Haller et al. |
| 2002/0013614 A1 | 1/2002 | Thompson |
| 2002/0021244 A1 | 2/2002 | Aizawa et al. |
| 2003/0171789 A1 | 9/2003 | Malek et al. |
| 2003/0172940 A1 | 9/2003 | Rogers et al. |
| 2003/0212440 A1 | 11/2003 | Boveja |
| 2004/0122487 A1 | 6/2004 | Hatlestad et al. |
| 2004/0215089 A1 | 10/2004 | Bergelson et al. |
| 2004/0249416 A1 | 12/2004 | Yun et al. |
| 2004/0267333 A1 | 12/2004 | Kronberg |
| 2005/0004628 A1 | 1/2005 | Goetz et al. |
| 2005/0021092 A1 | 1/2005 | Yun et al. |
| 2005/0038484 A1 | 2/2005 | Knudson et al. |
| 2005/0049655 A1 | 3/2005 | Boveja et al. |
| 2005/0065573 A1 | 3/2005 | Rezai |
| 2005/0070968 A1 | 3/2005 | Bergelson et al. |
| 2005/0075684 A1 | 4/2005 | Phillips et al. |
| 2005/0075693 A1 | 4/2005 | Toy et al. |
| 2005/0107841 A1 | 5/2005 | Meadows et al. |
| 2005/0113889 A1 | 5/2005 | Jimenez et al. |
| 2005/0131467 A1 | 6/2005 | Boveja |
| 2005/0131484 A1 | 6/2005 | Boveja et al. |
| 2005/0131485 A1 | 6/2005 | Knudson et al. |
| 2005/0131486 A1 | 6/2005 | Boveja et al. |
| 2005/0131487 A1 | 6/2005 | Boveja et al. |
| 2005/0131493 A1 | 6/2005 | Boveja et al. |
| 2005/0137644 A1 | 6/2005 | Boveja et al. |
| 2005/0143783 A1 | 6/2005 | Boveja et al. |
| 2005/0143786 A1 | 6/2005 | Boveja |
| 2005/0143787 A1 | 6/2005 | Boveja et al. |
| 2005/0143788 A1 | 6/2005 | Yun et al. |
| 2005/0149146 A1 | 7/2005 | Boveja et al. |
| 2005/0187590 A1 | 8/2005 | Boveja et al. |
| 2005/0192644 A1 | 9/2005 | Boveja et al. |
| 2005/0197678 A1 | 9/2005 | Boveja et al. |
| 2005/0209654 A1 | 9/2005 | Boveja et al. |
| 2005/0228693 A1 | 10/2005 | Webb et al. |
| 2005/0288736 A1 | 12/2005 | Persen et al. |
| 2006/0030891 A1 | 2/2006 | Saltzstein et al. |
| 2006/0052836 A1 | 3/2006 | Kim et al. |
| 2006/0074450 A1 | 4/2006 | Boveja et al. |
| 2006/0085040 A1 | 4/2006 | VanDanacker |
| 2006/0195152 A1 | 8/2006 | Gerber |
| 2006/0247711 A1 | 11/2006 | Verhoef et al. |
| 2007/0043411 A1 | 2/2007 | Foster et al. |
| 2007/0060916 A1 | 3/2007 | Pappone |
| 2007/0067000 A1 | 3/2007 | Strother et al. |
| 2007/0067004 A1 | 3/2007 | Boveja et al. |
| 2007/0106346 A1 | 5/2007 | Bergelson et al. |
| 2007/0191912 A1 | 8/2007 | Fischer et al. |
| 2007/0250121 A1 | 10/2007 | Miesel et al. |
| 2007/0270921 A1 | 11/2007 | Strother et al. |
| 2008/0015641 A1 | 1/2008 | Armstrong et al. |
| 2008/0097554 A1 | 4/2008 | Payne et al. |
| 2008/0132974 A1 | 6/2008 | Strother et al. |
| 2008/0221644 A1 | 9/2008 | Vallapureddy et al. |
| 2008/0300654 A1 | 12/2008 | Lambert et al. |
| 2008/0300656 A1 | 12/2008 | Donders et al. |
| 2008/0300657 A1 | 12/2008 | Stultz |
| 2008/0303480 A1 | 12/2008 | Prutchi et al. |
| 2009/0112291 A1 | 4/2009 | Wahlstrand et al. |
| 2009/0187230 A1 | 7/2009 | Dilorenzo |
| 2009/0259273 A1 | 10/2009 | Figueiredo et al. |
| 2009/0264966 A1 | 10/2009 | Blum et al. |
| 2010/0241183 A1 | 9/2010 | DiLorenzo |
| 2010/0256709 A1 | 10/2010 | Kallmyer |
| 2010/0256710 A1 | 10/2010 | Dinsmoor et al. |
| 2010/0268305 A1 | 10/2010 | Olson et al. |
| 2011/0004269 A1 | 1/2011 | Strother et al. |
| 2011/0004278 A1 | 1/2011 | Aghassian et al. |
| 2012/0022608 A1 | 1/2012 | Libbus et al. |
| 2012/0022617 A1 | 1/2012 | Tockman et al. |
| 2012/0053653 A1 | 3/2012 | Hiernaux et al. |
| 2012/0059431 A1 | 3/2012 | Williams et al. |
| 2012/0065698 A1 | 3/2012 | Errico et al. |
| 2012/0071946 A1 | 3/2012 | Errico et al. |
| 2012/0078319 A1 | 3/2012 | De Ridder |
| 2012/0083855 A1 | 4/2012 | Gross et al. |
| 2012/0101874 A1 | 4/2012 | Ben-Haim et al. |
| 2012/0136408 A1 | 5/2012 | Grill et al. |
| 2012/0232610 A1 | 9/2012 | Soffer et al. |

| | | |
|---|---|---|
| 2012/0239108 A1 | 9/2012 | Foutz et al. |
| 2012/0253378 A1 | 10/2012 | Makower et al. |
| 2012/0259380 A1 | 10/2012 | Pyles |

OTHER PUBLICATIONS

Invitation to Pay Additional Fees with Partial International Search cited in PCT/US2008/065386 mailed Aug. 28, 2008.
U.S. Non-Final Office Action mailed Dec. 8, 2010 in Lambert et al., U.S. Appl. No. 11/943,054, filed Nov. 20, 2007, and titled "Implantable Therapy System.".
U.S. Final Office Action cited in U.S. Appl. No. 11/943,054 mailed Apr. 6, 2011.
U.S. Non-Final Office Action mailed Feb. 11, 2011 in Donders et al., U.S. Appl. No. 11/943,069, filed Nov. 20, 2007, and titled Implantable Therapy System.
U.S. Non-Final Office Action cited in U.S. Appl. No. 11/943,093 mailed Jul. 7, 2011.
Kilgore, K. et al., "Nerve Conduction Block Utilising High-Frequency Alternating Current," *Medical & Biological Engineering & Computing*, vol. 42, pp. 394-406 (2004).
Product Brochure, "ATROSTIM Phrenic Nerve Stimulator," AtroTech Oy, P.O. Box 28, Fin-33721,Tampere, Finland, 2 pages (Jun. 2004).
Solomonow, M. et al., "Control of Muscle Contractile Force Through Indirect High-Frequency Stimulation," *American Journal of Physical Medicine*, vol. 62, No. 2, pp. 71-82 (1983).
Herrera, Miguel F., et al., "Intermittent Vagal Blocking with an Implantable Device Reduces Maximum Tolerated Volume (MTV) During a Standardized Nutrient Drink Test in Obese Subjects," AGA Institute, AASLD, SSAT, The 110th Annual Meeting of the AGA Institute: Digestive Disease Week May 30-Jun. 4, 2009, Chicago, IL, Gastroenterology vol. 136, No. 5, Suppl. 1 (May 2009).
Brancatisano, R., et al., "Implantation Technique of a Novel Vagal Blockade Medical Device for the Treatment of Obesity," IFSO-APC OSSANZ Conference 2008: Mar. 25-27, 2009, Hilton Cairns, Queensland Conference Program Handbook.
Toouli, M.D., James, et al., "Intra-Abdominal Vagal Blocking Reduces Calorie Intake, Enhances Satiation and Reduces Hunger during Significant and Sustained Weight Loss in Obese Subjects," Digestive Disease Week and the 109th Annual Meeting of the AGA Institute: May 17-22, 2008, San Diego, CA, Gastroenterology vol. 134, No. 4 (Suppl. 1) p. A-370 (Apr. 2008).
Tweden, Katherine S., et al. "Vagal Blocking for Obesity Control (VBLOC): Studies of Pancreatic Function and Safety in a Porcine Model," Obesity Surgery: Including Laparoscopy and Allied Care, Program Issue, World Congress, Australia, Aug. 30-Sep. 2, 2006. An International Surgical Journal for Research and Treatment of Massive Obesity, vol. 16, No. 8, p. 988, Aug. 2006.
Toouli, M.D., James, et al., "Vagal Blocking for Obesity Control (VBLOC): Effects on Excess Weight Loss, Calorie Intake, Satiation and Satiety," Obesity Surgery: Including Laparoscopy and Allied Care, Program Issue, World Congress, Porto, Sep. 5 to 8, 2007. An International Surgical Journal for Research and Treatment of Massive Obesity, vol. 17, No. 8, p. 1043 Aug. 2007.
Kow, M.D., Lilian, et al., "Comparison of Food Ingestion Disorders with Three Devices for Obesity," Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, vol. 18, No. 8, pp. 914-915 Aug. 2008.
Wilson, R.R., et al., "Intra-Abdominal Vagal Blocking Re3duces body Weight with Associated Reductions in Heart Rate and Without Adverse Effects on Electrocardiographic Parameters," Obesity Surgery: Including Laparoscopy and Allied Care, Program and Abstracts of the 13th World Congress of IFSO, Buenos Aires, Argentina, Sep. 24-27, 2008. An International Surgical Journal for Research and Treatment of Massive Obesity, vol. 18, No. 8, p. 923 Aug. 2008.
Kow, M.D., Lilian, et. al. "Selecting Vagal Blocking Electrical Algorithms for Obesity Treatment," Obesity Surgery: Including Laparoscopy and Allied Care, Program and Abstracts of the 13th World Congress of IFSO, Buenos Aires, Argentina, Sep. 24-27, 2008.
An International Surgical Journal for Research and Treatment of Massive Obesity, vol. 18, No. 8, p. 924, Aug. 2008.
Herrera, Miguel F., et al., "VBLOC and Improvements in Co-Morbidities in Obese Subjects During Weight Loss," Obesity Surgery: The Journal of Metabolic Surgery and Allied Care, Program and Abstracts of the 14th World Congress of IFSO, Paris, France, Aug. 26-29, 2009. An International Surgical Journal for Research and Treatment of Massive Obesity, vol. 19, No. 8, p. 983-984, Aug. 2009.
Herrera, Miguel F., et al., "Intermittent Vagal Blocking with an Implantable Device Reduces Maximum Tolerated Volume (MTV) During a Standardized Nutrient Drink Test in Obese Subjects," Obesity Surgery: The Journal of Metabolic Surgery and Allied Care, Program and Abstracts of the 14th World Congress of IFSO, Paris, France, Aug. 26-29, 2009. An International Surgical Journal for Research and Treatment of Massive Obesity, vol. 19, No. 8, p. 1012 Aug. 2009.
Brancastisano, Roy, et al., "Empower: A 12-Month Randomized, Prospective Clinical Trial: Safety and Effectiveness of VBLOC Therapy," 23rd Annual Scientific Conference of the Obesity Surgery Society of Australia and New Zealand, OSSANZ Conference 2010: The Changing Shape of Bariatrics, Nov. 10-12, Wednesday Nov. 10 10:30 am-12 noon, Tasmania Hotel Grand Chancellor, Hobart, Conference Program Handbook.
Kow, M.D., Lilian, et al., "Vagal Blocking Improves Obesity-Related Co-Morbidities in Obese Subjects with type 2 Diabetes Mellitus," 23rd Annual Scientific Conference of the Obesity Surgery Society of Australia and New Zealand , OSSANZ Conference 2010: The Changing Shape of Bariatrics, Nov. 10-12, Wednesday Nov. 10 3:30 pm-5:00 pm, Tasmania Hotel Grand Chancellor, Hobart, Conference Program Handbook.
Collins, Jane, et al., "Reduces Calorie Intake and Weight Loss during Vagal Block (VBLOC Therapy) in Morbidly Obese Patients with Type 2 Diabetes Mellitus," 23rd Annual Scientific Conference of the Obesity Surgery Society of Australia and New Zealand, OSSANZ Conference 2010: The Changing Shape of Bariatrics, Nov. 10-12, Thursday Nov. 11 10:30 am-12 noon, Tasmania Hotel Grand Chancellor, Hobart, Conference Program Handbook.
Toouli, M.D., James, et al., "Vagal Blocking: Treatment of Obesity Related type 2 Diabetes and blood Pressure—18 Month Results," 24th Annual Scientific Conference of the Obesity Surgery Society of Australia and New Zealand, OSSANZ Conference 2012: Bariatric surgery—more than an operation, Apr. 11-13, Wednesday Nov. 11 3:30 pm-5:00 pm, Northern Territory Darwin Convention Centre, Darwin, Conference Program Handbook.
Tweden, Katherine S., et al., "Vagal Blocking for Obesity Control (VBLOC): Studies of Pancreatic and Gastric Function and Safety in a Porcine Model," Plenary Session 2006/2 Surgery for Obesity and Related Diseases, Official Journal of the American Society for Bariatric Surgery, vol. 2, No. 3, pp. 301-302, May/Jun. 2006.
Camilleri, M.D., Michael, et al., "Selection of Electrical Algorithms to Treat Obesity with Intermittent Vagal Block Using an Implantable Medical Device," Surgery for Obesity and Related Diseases, Official Journal of the American Society for Bariatric Surgery, vol. 5, No. 2, pp. 224-229, Mar./Apr. 2009.
Herrera, Miguel F., et al., "Intermittent Vagal Blockade with an Implantable Device Improves Glycemic Control in Obese subjects with Type 2 Diabetes," 2009 Poster Session / Supplement to Surgery for Obesity and Related Diseases, Official Journal of the American Society for Bariatric Surgery, vol. 5, No. 3S, pp. S48-S49, May/Jun. 2009.
Herrera, Miguel F., et al., "Vagal Blocking Improves Glycemic Control and Blood Pressure in Subjects with Type 2 Diabetes and Hypertension," 2010 Plenary Session / Supplement to Surgery for Obesity and Related Diseases, Official Journal of the American Society for Bariatric Surgery, vol. 2, No. 3, pp. S1-S26, May/Jun. 2010.
Camilleri M.D., Michael, et al., "Vagal Blocking for Obesity control (VBLOC): Plasma Pancreatic Polypeptide (PPP) Response to a Standardized Sham Meal Challenge," The Obesity Society 2007 Annual Scientific Meeting, Oct. 20-24, 2007, New Orleans Louisiana. Supplement to Obesity, vol. 15, Program Abstract Supplement, Sep. 2007.

Camilleri, M.D., Michael, et al., "Intra-abdominal Vagal Blocking (VBLOC therapy): Clinical Results with a New Implantable Medical Device," Surgery, vol. 143, No. 6, pp. 723-731, Jun. 2008.

Kow, M.D., Lilian, et al., "Vagal Blocking for the Treatment of Obesity Delivered Using the Fully Implantable Maestro Rechargeable System: 12 Month Results," Surgery for Obesity and Related Diseases: Emerging Technologies Session 2011, 7, pp. 363-364, (2011).

Sarr, M.G., et al., "The EMPOWER Study: Randomized, Prospective, Double-Blind, Multicenter Trial of Vagal Blockade to Induce Weight Loss in Morbid Obesity," Obes. Surg. Published Sep. 8, 2012, (12pp) Springer Science+Business Media, LLC (2012).

Tweden, Katherine S., et al., "Vagal Blocking Treatment of Obesity Related Type 2 Diabetes and Blood Pressure—18 Month Results,"5th Congress of the International Federation for the surgery of Obesity and Metabolic Disorders European Chapter (IFSO-EC), Barcelona '12, Apr. 26-28, 2012.

Toouli, M.D., James, et al., "Vagal Blocking for Obesity Control (VBLOC): Interim Six Months Results in an ongoing Trial Using a Second Generation System," 2008 Scientific Session of the Society of American Gastrointestinal and Endoscopic (SAGES), Philadelphia, Pennsylvania, USA Apr. 9-12, 2008. Poster Presentations, Surgical Endoscopy (2008) 22, p. S194, Springer Science+Business Media, LLC (2008).

Toouli, M.D., James, et al., "Vagal Blocking for Obesity Control (VBLOCTM): Ongoing Comparison of Weight Loss with Two Generations of an Active, Implantable Medical Device," 2008 Plenary Session II / Surgery for Obesity and Related Diseases, Official Journal of the American Society for Bariatric Surgery, e t al., vol. 4, No. 3, p. 305, May/Jun. 2008.

Waataja, Jonathan J., et al., "Effects of High-Frequency Alternating Current on Axonal Conduction Through the Vagus Nerve," Journal of Neural Engineering Neural Eng. 8 (2011) (1741-1747) IOP Publishing Ltd, (2011) online at stacks.iop.org.

Kow, M.D., Lilian, et al., "Comparison of Food Ingestion disorders with Three Devices for Obesity Treatment," and Wilson, Richard, et al., "Intra-abdominal Vagal Blocking Reduces Body Weight with Associated Reductions in Heart Rate and Without Adverse Effects on Electrocardiographic Parameters," TOS 2008 Abstract Supplement / Poster Session 2 Abstracts, vol. 16, Supp. 1: S222, Oct. 2008 www.obesityjournal.org.

Herrera, Miguel F., et al., "Treatment of Obesity-Related Type 2 Diabetes with Vagal Blocking," Obesity 2011 Abstract Supplement / Poster Abstracts—Monday, Oct. 3, 2011, Obesity vol. 19, sup. 1:S185, Nov. 2011, www.obsesityjournal.org.

Wray, N., et al., "Reduced Calorie Intake and Weight Loss During Vagal Blocking in Subjects with Obesity-Related Type 2 Diabetes Mellitus," Obesity 2011 Abstract Supplement / Poster Abstracts—Monday, Oct. 3, 2011, Obesity vol. 19, Supp. 1:S190, Nov. 2011, www.obesityjournal.org.

Toouli, M.D., James, et al., "Reduced Calorie Intake and Weight Loss During Vagal Bloc (VBLOC Therapy) in Morbidly Obese Patients with Type 2 Diabetes Mellitus," Gastroenterology 2011, vol. 140: S-619, AGA Institute.

Tweden, Katherine S., et al., "Vagal Blocking for Obesity Control (VBLOC): Concordance of Effects of Very High Frequency Blocking Current At the Neural and Organ Levels Using Two Preclinical Models," Gastroenterology 2006, vol. 130 (suppl2 2) A-148, AGA Institute.

Kow, M.D., Lilian, et al., "An Implantable Vagal Blocking System to Treat Obesity: Laparoscopic Implantation Technique and Early Results in a proof-of-Principle Clinical Study,", SAGES 2008 Emerging Technology Oral Abstracts, p. 295, www.sages.org.

Toouli, M.D., James, et al., "Treatment of Obesity-Related Co-Morbidities with VBLOC Therapy," Obes. Surg. 21:998, Springer Science+Business Media, LLC (2011).

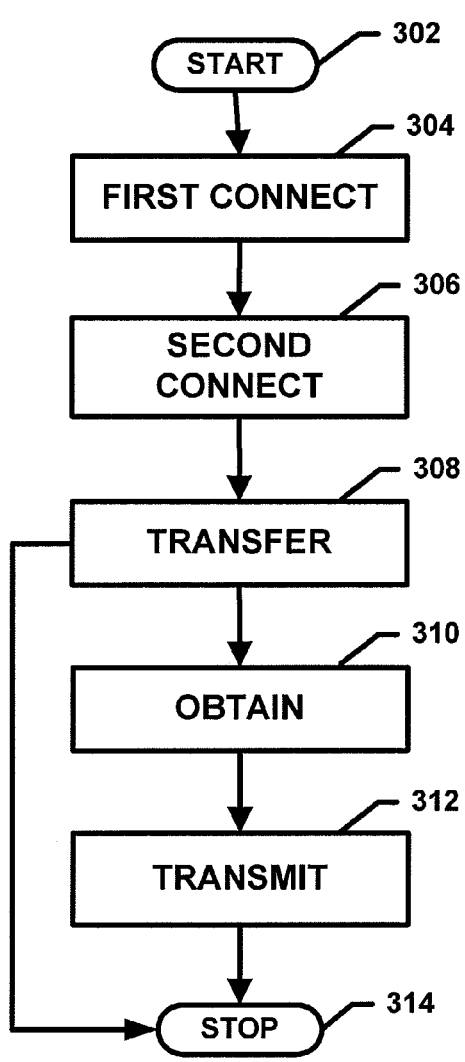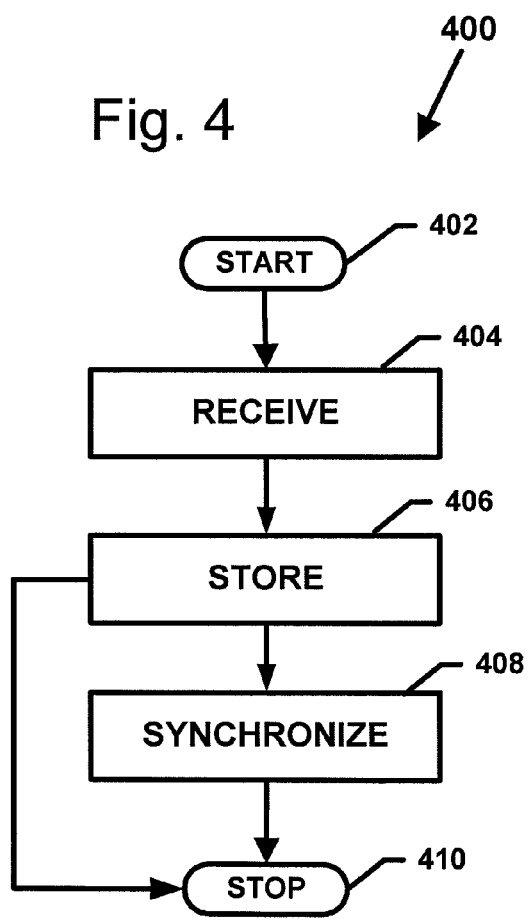

Patient Use Report

| Report Date | Patient Use | Transmit Coil Not Connected | Transmit Coil Not Positioned Correctly | Patient Non-Use – Controller Not Charged | Controller was Charging | Unknown |
|---|---|---|---|---|---|---|
| 1/15/2007 | 0.00% | 0.00% | 0.00% | 0.00% | 0.00% | 0.00% |
| 1/16/2007 | 0.00% | 0.00% | 0.00% | 0.00% | 0.00% | 0.00% |
| 1/17/2007 | 0.00% | 0.00% | 0.00% | 0.00% | 0.00% | 0.00% |
| 1/18/2007 | 55.98% | 0.49% | 0.42% | 0.00% | 0.06% | 43.04% |
| 1/19/2007 | 46.62% | 0.01% | 0.18% | 0.00% | 52.73% | 0.46% |
| 1/20/2007 | 5.39% | 0.49% | 0.00% | 0.00% | 0.00% | 94.12% |
| 1/21/2007 | 57.65% | 3.23% | 0.10% | 0.00% | 0.00% | 39.02% |
| 1/22/2007 | 97.49% | 0.27% | 0.15% | 0.00% | 0.00% | 2.09% |
| Average | 32.89% | 0.6% | 0.1% | 0.1% | 6.6% | 22.3% |

Patient Use Details Report

| 1/21/2007 | Patient Use | Transmit Coil Not Connected | Transmit Coil Not Positioned Correctly | Controller Not Charged | Controller was Charging | Unknown |
|---|---|---|---|---|---|---|
| | | | | Patient Non-Use | | |
| 12:00:00 AM | 0.00% | 0.00% | 0.00% | 0.00% | 0.00% | 100.00% |
| 1:00:00 AM | 0.00% | 0.00% | 0.00% | 0.00% | 0.00% | 100.00% |
| 8:00:00 AM | 0.00% | 0.00% | 0.00% | 0.00% | 0.00% | 100.00% |
| 9:00:00 AM | 0.00% | 0.00% | 0.00% | 0.00% | 0.00% | 100.00% |
| 10:00:00 AM | 0.00% | 45.81% | 0.00% | 0.00% | 0.00% | 54.19% |
| 11:00:00 AM | 88.47% | 9.83% | 1.69% | 0.00% | 0.00% | 0.00% |
| 12:00:00 PM | 100.00% | 0.00% | 0.00% | 0.00% | 0.00% | 0.00% |
| 1:00:00 PM | 100.00% | 0.00% | 0.00% | 0.00% | 0.00% | 0.00% |
| 2:00:00 PM | 100.00% | 0.00% | 0.00% | 0.00% | 0.00% | 0.00% |
| 3:00:00 PM | 99.97% | 0.00% | 0.00% | 0.00% | 0.00% | 0.03% |
| 4:00:00 PM | 100.00% | 0.00% | 0.00% | 0.00% | 0.00% | 0.00% |
| 5:00:00 PM | 100.00% | 0.00% | 0.00% | 0.00% | 0.00% | 0.00% |
| 6:00:00 PM | 100.00% | 0.00% | 0.00% | 0.00% | 0.00% | 0.00% |
| 7:00:00 PM | 100.00% | 0.00% | 0.00% | 0.00% | 0.00% | 0.00% |
| 8:00:00 PM | 99.97% | 0.00% | 0.00% | 0.00% | 0.00% | 0.03% |
| 9:00:00 PM | 6.06% | 0.00% | 0.00% | 0.00% | 0.00% | 93.94% |
| 10:00:00 PM | 0.00% | 0.00% | 0.00% | 0.00% | 0.00% | 100.00% |
| 11:00:00 PM | 0.00% | 0.00% | 0.00% | 0.00% | 0.00% | 100.00% |

Patient ID: 01353

| SUMMARY | THERAPY | DIAGNOSTICS | REPORTS | CONFIGURATION | REGISTRATION |

From Date: Monday, January 15, 2007    To Date: Monday, January 22, 2007

- Patient Use
- Therapy Delivery
- Battery Charge
- Lead Status
- Therapy History

Therapy Delivery Report — 1301

| Date | Therapy Delivery | Patient Non-Use 1320 | | | Therapy Non-Delivery 1350 | | | | |
| --- | --- | --- | --- | --- | --- | --- | --- | --- | --- |
| | | Coil Not Connected | Coil Not Positioned | Controller Not Charged | Controller was Charging | Coil Shorted | Wrong Coil | Impedance Out of Range | Link Error | System Error |
| 1/15/2007 | 0.00% | 0.00% | 0.00% | 0.00% | 0.00% | 0.00% | 0.00% | 0.00% | 0.00% | 0.00% |
| 1/16/2007 | 0.00% | 0.00% | 0.00% | 0.00% | 0.00% | 0.00% | 0.00% | 0.00% | 0.00% | 0.00% |
| 1/17/2007 | 0.00% | 0.00% | 0.00% | 0.00% | 0.00% | 0.00% | 0.00% | 0.00% | 0.00% | 0.00% |
| 1/18/2007 | 38.45% | 0.10% | 1.20% | 0.00% | 0.13% | 0.00% | 0.00% | 0.00% | 10.53% | 0.00% |
| 1/19/2007 | 35.40% | 0.00% | 0.65% | 0.00% | 52.78% | 0.00% | 0.00% | 0.00% | 0.00% | 0.02% |
| 1/20/2007 | 5.87% | 0.00% | 0.00% | 0.00% | 0.00% | 0.00% | 0.00% | 0.00% | 0.00% | 0.00% |
| 1/21/2007 | 22.73% | 3.39% | 0.00% | 0.00% | 0.00% | 0.00% | 0.00% | 0.00% | 1.94% | 0.00% |
| 1/22/2007 | 41.2?% | 0.00% | 0.?3% | 0.00% | 6.11% | 0.00% | 0.00% | 0.00% | 0.00% | 0.00% |
| Average: | 17.96% | 0.44% | 0.?3% | 0.00% | 6.11% | 0.00% | 0.00% | 0.00% | 1.55% | 0.00% |

Run Report

REMOTE MONITORING AND CONTROL OF IMPLANTABLE DEVICES

CROSS REFERENCE TO RELATED APPLICATIONS

This application is a continuation of application Ser. No. 11/716,353, filed Mar. 9, 2007, now U.S. Pat. No. 8,068,918, Nov. 29, 2011, which application is incorporated herein by reference in its entirety.

BACKGROUND OF THE INVENTION

1. Field of the Invention

This invention pertains to monitoring and controlling therapeutic treatment. More particularly, this invention pertains to remotely monitoring and controlling therapeutic devices.

2. Description of the Prior Art

FIG. 1 illustrates a conventional therapeutic system 100 including an implantable device (i.e., a regulator) 110 and an external unit (i.e., a programmer) 130. The device 110 is typically implanted within a body of a patient to provide treatment for a disorder. For example, in conventional cardiac rhythm management systems, the implanted device 110 is an autonomous device connected to the heart of a patient to provide electrical signals to regulate the heartbeat of the patient. Alternatively, the implanted device 110 can be connected to nerves of the patient to apply electrical signals to up-regulate or down-regulate neural activity on the nerves (e.g., the vagal nerves).

The implanted device 110 can record a treatment history of the patient. In such embodiments, the implanted device includes a memory 112 in which the treatment history (i.e., a record of events) can be stored. Examples of typical events stored in a treatment history include delivery of treatment to the patient, an attempt to transmit information to the external unit 130, and receipt of information from the external unit 130.

In general, the external unit 130 is operated by a clinician (e.g., a doctor or other practitioner). The clinician can load treatment programs (i.e., instructions specifying the treatment regimen for the patient) onto the implanted device 110 using the external unit 130. The external unit 130 also can download the stored treatment history from the implanted device 110 and can transfer this history over a network 140 to a computing device 150, such as a server, for storage on memory 152.

Typically, the external unit 130 can communicate with the implanted device 110 when in proximity to the device 110. For example, the external unit 130 can connect to the implanted device 110 through a radio-frequency (RF) link. To change a patient's treatment schedule, update software on the implanted device 110, or obtain the stored treatment history, therefore, a patient must visit the clinician's office or the clinician must travel to see the patient.

The conventional therapeutic system 100 shown in FIG. 1 also can include an optional controller unit 120. A patient can utilize the controller unit 120 to manage the operation of the implanted device 110. For example, if the therapeutic system 100 is a pain management system, then a patient can use the controller unit 120 to increase or decrease the dosage or frequency of treatment. The controller unit 120 also can provide power to the implanted device 110. For example, in an embodiment, the implanted device 110 provides treatment only when power is received from the controller unit 120.

The controller unit 120 also can monitor the performance of the implanted device 110 and can collect information from the implanted device 110. In such embodiments, the controller 120 can include a memory 122 for storing the treatment history. The controller unit 120 is generally configured to communicate with the regulator 110 (e.g., via an RF signal). In such embodiments, the implanted device 110 may not include a memory. Rather, event indications can be transmitted to the controller unit 120 from the implanted device 110 as the events occur.

In some systems, the external unit 130 communicates with the controller 120 instead of the implanted device 110. Typically, in such systems, the external unit 130 is placed in physical proximity to the controller 120 to communicate with the controller 120. For example, the external unit 130 can communicate with the controller unit 120 through a cable connection (e.g., via a USB port) or an RF communication link. Here as well, a patient visits the clinician's office or the clinician travels to see the patient to transfer data between the clinician and the controller 120.

One conventional therapeutic system is described in U.S. Pat. No. 6,564,102 to Boveja. The '102 patent discloses an implanted device for use in neuromodulation therapy for coma and brain injury. The '102 patent also discloses an external device that may have a telecommunications module to control predetermined programs remotely. Treatment parameter data can be viewed remotely by medical personnel via a server on a personal computer or a Palm Pilot. U.S. Publication No. 2005/0131467 to Boveja extends this concept to remote programming and data exchange over a wide area network, and U.S. Publication No. 2005/0131484 describes remotely interrogating and programming an implanted device over a wide area network.

SUMMARY OF THE INVENTION

This invention consists of therapeutic systems and methods for remotely monitoring and/or controlling therapeutic devices.

The principal components of the system include a therapeutic device (i.e., a regulator) implanted within a patient and an external data transfer device (DTD) for providing a communications link between the regulator and a remote device. For example, the external DTD can provide data transmission between the regulator and a remote computer, a remote clinician programmer, or another remote device.

According to aspects of the invention, data synchronization can be provided by compiling patient treatment information in patient databases on a remote computing device and transferring the compiled information pertaining to one or more patients to a requesting clinician programmer.

According to other aspects of the invention, patient reports can be generated based on the compiled patient information and displayed to clinicians to aid in treatment analysis.

According to still other aspects of the invention, software updates for the therapeutic devices in the therapeutic system can be provided automatically from a remote computing device.

According to still other aspects of the invention, voice data and/or informational data can be transferred between the clinician and the patient, even when the clinician and patient are situated in remote locations from one another.

In some embodiments, the external DTD also can operate the implanted regulator.

In other embodiments, the therapeutic system includes a separate controller unit enabling the patient to operate/manage the implanted regulator.

BRIEF DESCRIPTION OF THE DRAWINGS

FIG. 3 is a flowchart illustrating a communication process implemented by the DTD to transfer patient information from a controller to a remote computing device in accordance with the principles of the present invention;

FIG. 4 shows an operational flow of a complementary logic process followed by the remote computing device during the execution of portions of the communication process of FIG. 3 in accordance with the principles of the present invention;

FIG. 10 illustrates an example embodiment of a patient use report indicating whether the patient correctly used the treatment system over a period of time in accordance with the principles of the present disclosure;

FIG. 12 illustrates an exemplary daily patient usage report indicating whether the patient correctly used the treatment system over the course of a given day in accordance with the principles of the present disclosure;

FIG. 13 is an exemplary therapy delivery report including a table indicating for each day within a range of days whether treatment was delivered during a scheduled delivery time and, if not, why treatment was not delivered in accordance with the principles of the present disclosure;

DETAILED DESCRIPTION OF THE PREFERRED EMBODIMENTS

The following commonly assigned and copending U.S. patent applications are incorporated herein by reference: U.S. Publication No. 2008/0300656, A1, published Dec. 4, 2008; U.S. Publication No. 2005/0131485 A1, published Jun. 16, 2005; U.S. Publication No. 2005/0038484 A1, published Feb. 17, 2005; U.S. Publication No. 2004/0172088 A1, published Sep. 2, 2004; U.S. Publication No. 2004/0167583 A1, published Aug. 26, 2004; U.S. Publication No. 2004/0172085 A1, published Sep. 2, 2004; U.S. Publication No. 2004/0176812 A1, published Sep. 9, 2004; and U.S. Publication No. 2004/0172086 A1, published Sep. 2, 2004.

With reference now to the various drawing figures in which identical elements are numbered identically throughout, a description of the preferred embodiment of the present invention will now be described. In the preferred embodiment, the invention is described with reference to use of a treatment system including a therapeutic device (i.e., a regulator) implanted within a patient and an external data transfer device (DTD) for providing bi-directional communication between the regulator and remote devices. It will be appreciated the teachings of the present disclosure could be applied to any implantable apparatus for dispensing a therapeutic treatment to a patient.

For example, the invention can pertain to treatments of disorders associated, at least in part, with neural activity. These may include, without limitation, gastrointestinal disorders (including obesity) and pancreo-biliary disorders. Alternatively, the invention can pertain to treatments of disorders associated, at least in part, with muscular activity.

Figure 2:
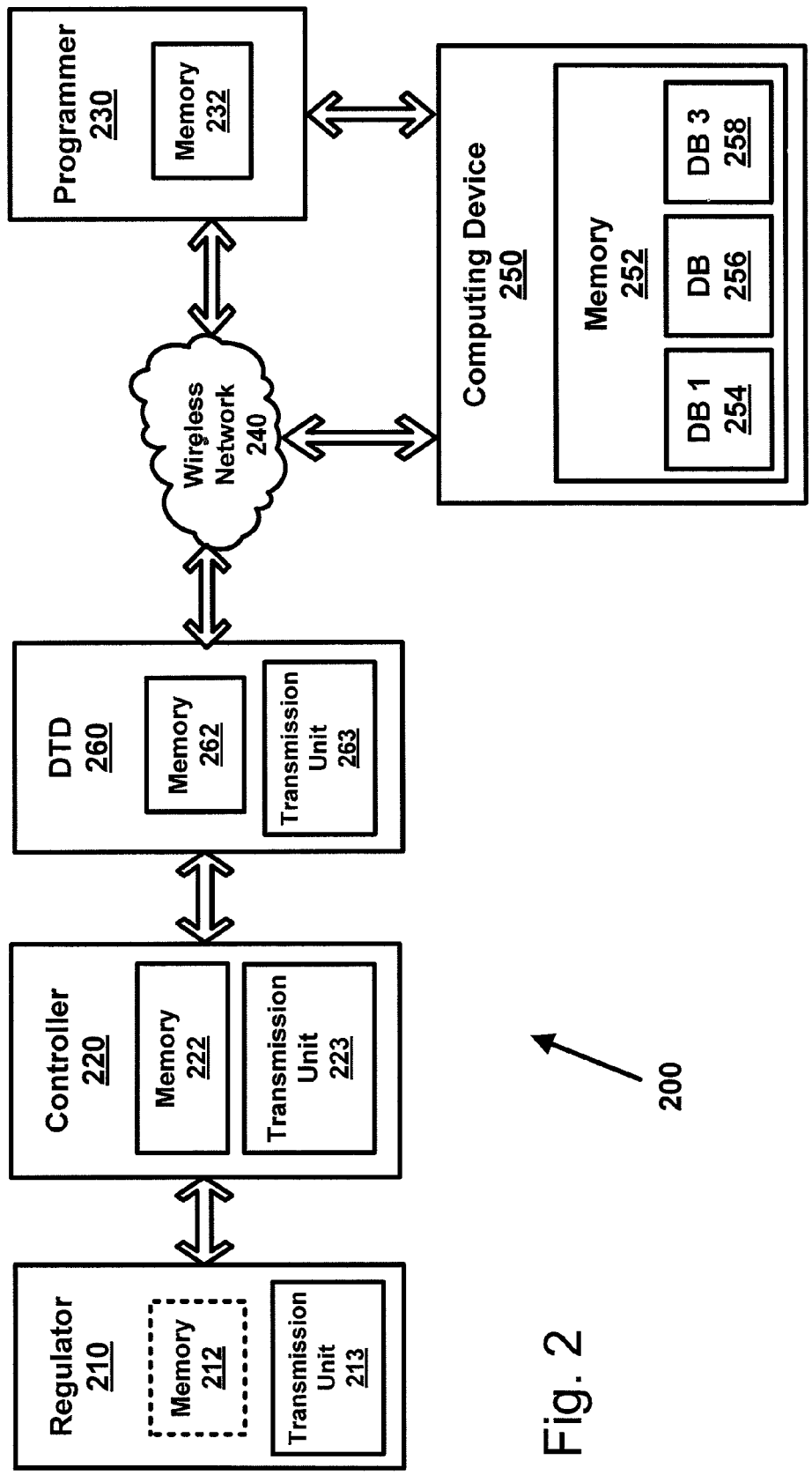
FIG. 2 is a block diagram generally illustrating an exemplary treatment system including a regulator, a controller, and a DTD configured in accordance with the principles of the present invention.

The present invention and its benefits can be better appreciated with a description of preferred embodiments, which will now be described with reference to FIGS. 2-18. FIG. 2 is a block diagram generally illustrating an exemplary treatment system 200 including a regulator 210, a controller 220, and a data transfer device (DTD) 260 configured in accordance with the principles of the present invention. The treatment system 200 also can include a programmer 230 and/or a computing device 250 on which data (e.g., patient information, software updates, etc.) can be stored, processed, and/or accessed.

Figure 1:
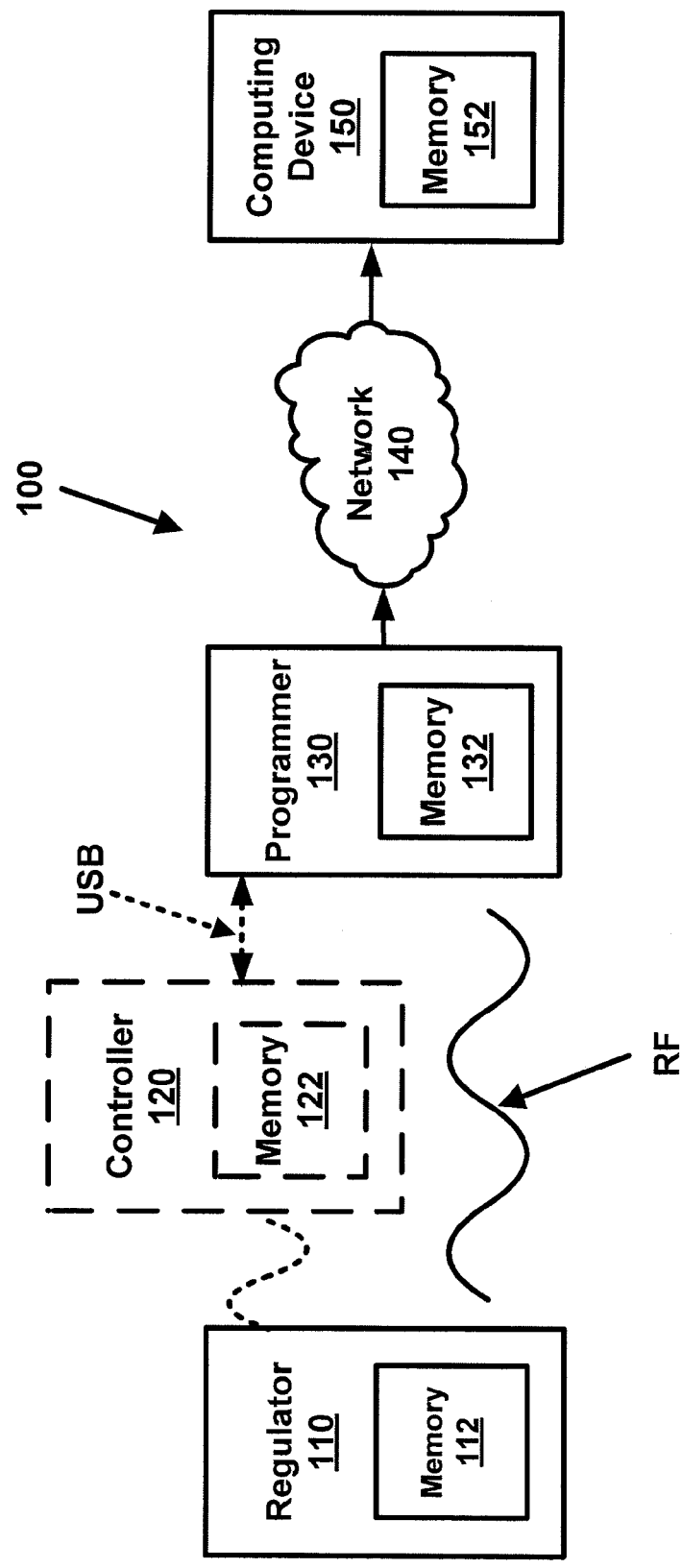
FIG. 1 illustrates a conventional therapeutic system including an implantable device and an external unit.

In an embodiment, the controller 220 and the regulator 210 are generally the same as the controller 120 and the regulator 110 of FIG. 1. In other embodiments, the regulator 210 may not include a memory 212 in which events can be stored and time-stamped. In such embodiments, indications of events are transmitted from the regulator 210 to the controller 220 or the DTD 260 for storage as they occur. Examples of treatment events to be stored can include, without limitation, treatment delivery events, patient use events, and battery charging events. Further details describing the types of events stored are provided herein.

The DTD 260 can be any type of data transfer device that is capable of wirelessly communicating with the controller 220 (or the regulator 210) and transferring (e.g., downloading/ uploading) electronic information to remote locations. In a preferred embodiment, the DTD 260 is a mobile device. Non-limiting examples of the DTD 260 include a personal computer, a notebook computer, a cellular phone, a personal digital assistant (PDA), a smart phone, etc.

The DTD 260 can communicate with the controller 220 using a cable connection (e.g., a USB cable, SCSI cable, coaxial cable, phone cable, etc.). In other embodiments, the DTD 260 can communicate with the controller 220 using a wireless connection. For example, the DTD 260 can communicate with the controller 220 over an RF signal or a CDMA signal. The controller 220 typically communicates with the regulator 210 via an RF signal. In an alternative embodiment, the DTD 260 communicates directly with the regulator 210 using a wireless signal (e.g., an RF signal).

The programmer 230 is generally the same as the programmer 130 disclosed in FIG. 1, except the programmer 230 is configured to communicate with the DTD 260 remotely to obtain information from and transmit information to the regulator 210. For example, the DTD 260 can communicate with the programmer 230 to receive treatment instructions and/or software updates from the programmer memory 232. The DTD 260 also can transmit to the programmer 230 a treatment history identifying treatment events and indicating when each event took place. In an embodiment, the programmer 230 is configured to communicate with the DTD 260 over a wireless network. In other embodiments, the programmer 230 is configured to communicate with the DTD 260 using any desired communication link.

The DTD 260 also can communicate with the computing device 250. In some embodiments, the computing device 250 can include a single computing device, such as a server computer. In other embodiments, the computing device 250 can include multiple computing devices configured to communicate with one another over a network (not shown). The computing device 250 can store multiple databases within memory 252. The databases stored on the computing device 250 can be organized by clinic, practicing clinician, programmer identification code, or any other desired category.

In the example shown, the computing device 250 stores a first, second, and third database 254, 256, 258, respectively, in memory 252. Each database 254, 256, 258 can be associated with a particular patient. Each patient database 254, 256, 258 stores treatment history data, such as the treatment events and patient use events (described in greater detail herein), obtained from the DTD 260 of the respective patient. As will be recognized by one of skill in the art, each database 254, 256, 258 can be configured according to a relational model, a hierarchal model, a network model, or any other desired database model.

In an embodiment, the computing device 250 is configured to communicate with the programmer 230 via the network 240. In another embodiment, the computing device 250 is configured to communicate with the programmer 230 directly.

Data Synchronization

In general, the remote computing device 250 provides a global repository for patient information. The computing device 250 can receive patient information from multiple programmers 230 and/or multiple DTD's 260. A clinician can access the computing device 250 and obtain treatment information for one or more patients using a programmer 230. In an embodiment, a single programmer 230 also can be shared among multiple clinicians (e.g., among clinicians working in the same office).

Each programmer 230 is configured to access the computing device 250 to obtain patient information from one or more patient databases when desired by a clinician. All or part of the information contained in a given patient database can be transferred to the programmer 230 upon request. The programmer 230 can store this information in memory 232 for later use by the clinician. Storing the patient information on the programmer 230 enables the clinician to access the information at any time, even when the programmer 230 is not communicatively linked to the computing device 250.

In some embodiments, each programmer 230 can determine whether the programmer 230 has all relevant patient information stored in its memory 232. For example, the programmer 230 can determine treatment data is missing (e.g., by comparing the date on which treatment was initiated, the current date, and the dates for which a treatment history is recorded). If gaps exist in the treatment history stored on the programmer 230, then the programmer 230 can initiate communication with the computing device 250 to request the relevant information.

Such a synchronization process enables the clinician to switch programmers 230 (e.g., if the original programmer 230 ceases to function) without losing patient data. Enabling data synchronization between the computing device 250 and the programmers 230 also provides greater freedom to patients in choosing treating clinicians. For example, if a patient wishes to obtain treatment from a different clinician (e.g., due to job relocation, change in healthcare, desire to change clinicians, etc.), then the patient can choose any clinician capable of accessing the computing device 250. The new clinician can continue patient treatment relatively uninterrupted by synchronizing patient data between the clinician's programmer 230 and the computing device 250.

The chosen clinician can use the clinician's programmer 230 to obtain the patient treatment history from the computing device 250. Armed with the patient's treatment history, the chosen clinician can begin treating the patient without significant delay. Patients need not worry about collecting the relevant documents from the original clinician or waiting for the original clinician to find the time to transfer the information to the new clinician.

Initiating Treatment

When using a therapeutic system configured in accordance with the principles of the present invention, the patient will not necessarily need to travel to the clinician's office, hospital, or other such location to initiate a treatment regimen. The clinician can upload a treatment program to the patient's controller 220 from a remote location through the DTD 260. For example, the clinician can transfer a treatment program to the DTD 260 from the programmer 230 or from the computing device 250. Alternatively, if it is desired for the clinician to be in proximity to the patient during the initiation process, the controller 220 can be connected to the programmer 230 through a cable or a wireless connection.

To initiate the treatment regimen, the clinician downloads a treatment specification and a therapy schedule to the patient's controller 220 or directly to the regulator 210. In general, the treatment specification indicates configuration values for the regulator 210 and optionally for the controller 220. For example, in the case of vagal nerve treatment for obesity, the treatment specification can define the amplitude, frequency, and pulse width for the electrical signals emitted by the implanted regulator 210. In another embodiment, "ramp up" time (i.e., the time period during which the electrical signals builds up to the desired amplitude) and "ramp down" time (i.e., the time period during which the signals decrease from the desired amplitude to about zero) can be specified.

The therapy schedule indicates an episode start time and an episode duration for at least one day of the week. An episode refers to the administration of therapy over a discrete period of time. Preferably, the clinician programs an episode start time and duration for each day of the week. In an embodiment, multiple episodes can be scheduled within a single day. Therapy also can be withheld for one or more days at the determination of the clinician.

During a therapy episode, the regulator 210 completes one or more treatment cycles in which the regulator 210 sequences between an "on" state and an "off" state. For the purposes of this disclosure, a treatment cycle includes a time period during which the regulator 210 continuously emits treatment (i.e., the "on" state) and a time period during which the regulator 210 does not emit treatment (i.e., the "off" state). Typically, each therapy episode includes multiple treatment cycles. The clinician can program the duration of each treatment cycle. In an embodiment, the clinician can program the length of time over which the regulator is configured in the "on" state and the length of time over which the regulator is configured in the "off" state.

When configured in the "on" state, the regulator 210 continuously applies treatment (e.g., emits an electrical signal). The regulator 210 is cycled to an "off" state, in which no signal is emitted by the regulator 210, at intermittent periods to mitigate the chances of triggering a compensatory mechanism by the body. For example, if a continuous signal is applied to a patient's nerve for a sufficient duration, the patient's brain eventually can learn to develop an alternate nerve pathway to transmit the signal.

Follow-Up Treatment

Treatment history and other desired information stored by the controller 220 or regulator 210 can be sent to the remote computing system 250 or another data storage device. For example, FIG. 3 is a flowchart illustrating a communication process 300 implemented by the DTD 260 to transfer patient information from the controller 220 to the computing device 250 in accordance with the principles of the present invention.

The communication process 300 initializes and begins at a start module 302 and proceeds to a first connect operation 304. The first connect operation 304 communicatively couples the DTD 260 to the controller 220. For example, the first connect operation 304 can connect a transmission unit 263 of the DTD 260 to a transmission unit 223 of the controller 220 via a cabled connection, a wireless local area network (WLAN or Wi-Fi) connection, a wireless personal area network (WPAN) connection, e.g., BLUETOOTH®, or any desired communication link.

A second connect operation 306 communicatively couples the DTD 260 to the computing device 250. For example, the DTD 260 can communicate with the computing device 250 over a network 240 (e.g., a wireless network including a cellular network, a local area network (LAN), a wide area network (WAN), etc.). In other embodiments, the second connect operation 306 can couple the DTD 260 directly with the computing device 250.

A transfer operation 308 transmits treatment data (e.g., the identity and timing of treatment events) from the controller 220 or regulator 210 to the computing device 250 via the DTD 260. In an embodiment, the transfer operation 308 obtains the stored treatment events from the controller memory 222 (FIG. 2) and transmits the stored events to the DTD 260. The DTD 260 then transmits the obtained treatment data to the computing device 250. For example, the transfer operation 308 can obtain patient use data, therapy delivery data, and/or battery charge data and send this data to the computing device 250 for storage. In an embodiment, the transfer operation 308 encrypts the data before transmitting the data between the devices 220, 260, 250 in treatment system 200. The communication process 300 can complete and end at a stop module 314.

In another embodiment, however, an optional obtain operation 310 implemented by the DTD 260 receives or downloads from the computing device 250 a new set of therapy parameters and/or a new therapy schedule. A transmit operation 312 sends the obtained data to the controller 220 to upload to the regulator 210. The communication process 300 completes and ends at the stop module 314. In alternative embodiments, the DTD 260 implements communication process 300 directly with the regulator 210 without using the controller 220 as an intermediary.

FIG. 4 shows an operational flow of a complementary logic process 400 followed by the computing device 250 during the execution of portions of the communication process 300. The logic process 400 initializes and begins at a start module 402 and proceeds to a receive operation 404. The receive operation 404 obtains from the DTD 260 data associated with a particular patient. In an embodiment, the receive operation 404 obtains data indicating operation details of the therapeutic regulator 210 over a period of time. In another embodiment, the receive operation 404 obtains data indicating when therapy was delivered to the patient.

The receive operation 404 can be initiated by the DTD 260. For example, the DTD 260 can be configured to immediately upload the patient information to the computing device 250 after receiving the patient information from the controller 220 or from the regulator 210. Alternatively, the DTD 260 can be instructed by the programmer 230 (i.e., the clinician) to upload the patient information to the computing device 250. In other embodiments, the computing device 250 can initiate implementation of the receive operation 404. For example, the computing device 250 can periodically communicate with the DTD 260 to request updates of patient information.

A store operation 406 adds the newly obtained data to one or more databases stored on the computing device 250. For example, treatment data pertaining to a given patient can be stored in a database associated with the given patient. If the computing device 250 does not include a database associated with the particular patient, then the store operation 406 generates a new patient database in which to store the information. As will be discussed herein, each patient database can include a log indicating when the therapeutic regulator 210 was operational, when treatment was delivered, and when and/or why treatment failed. In some embodiments, the logic process 400 completes and ends at a stop module 410.

In other embodiments, the logic process 400 proceeds to a synchronize operation 408, which sends the generated/updated patient database (e.g., DB1 254) automatically from the computing device 250 to the programmer 230 of the appropriate clinician. Alternatively, the synchronization operation 408 can provide the patient information to the programmer 230 only upon receiving a synchronization request from the programmer 230. The logic process 400 completes and ends at a stop module 410 as discussed above.

In an example embodiment, the synchronize operation 408 described above can upload the patient database automatically to the programmer 230 via a direct connection. In another embodiment, the synchronize operation 408 can upload the patient database to the programmer 230 over a network 240. In yet another embodiment, the synchronize operation 408 can send the patient database to the programmer 230 via email, a file transfer protocol (FTP) request, an HTTP request, or any other data transfer mechanism.

The transferred patient information can be useful in a number of applications in addition to data synchronization, as will be described in greater detail herein.

Patient Reports

Patient reports can be generated, e.g., by the programmer 230 or by the computing device 250, based on the compiled information stored on the computing device 250. In general, patient reports organize and format compiled treatment information and/or system usage information to aid the clinician in determining the success of the treatment, identifying issues hindering treatment, and/or counseling patients in effective use of the treatment system 200. Non-limiting examples of patient reports include a therapy delivery report, a therapy history report, a patient use report, a battery status report, and a lead status report.

Figure 5:
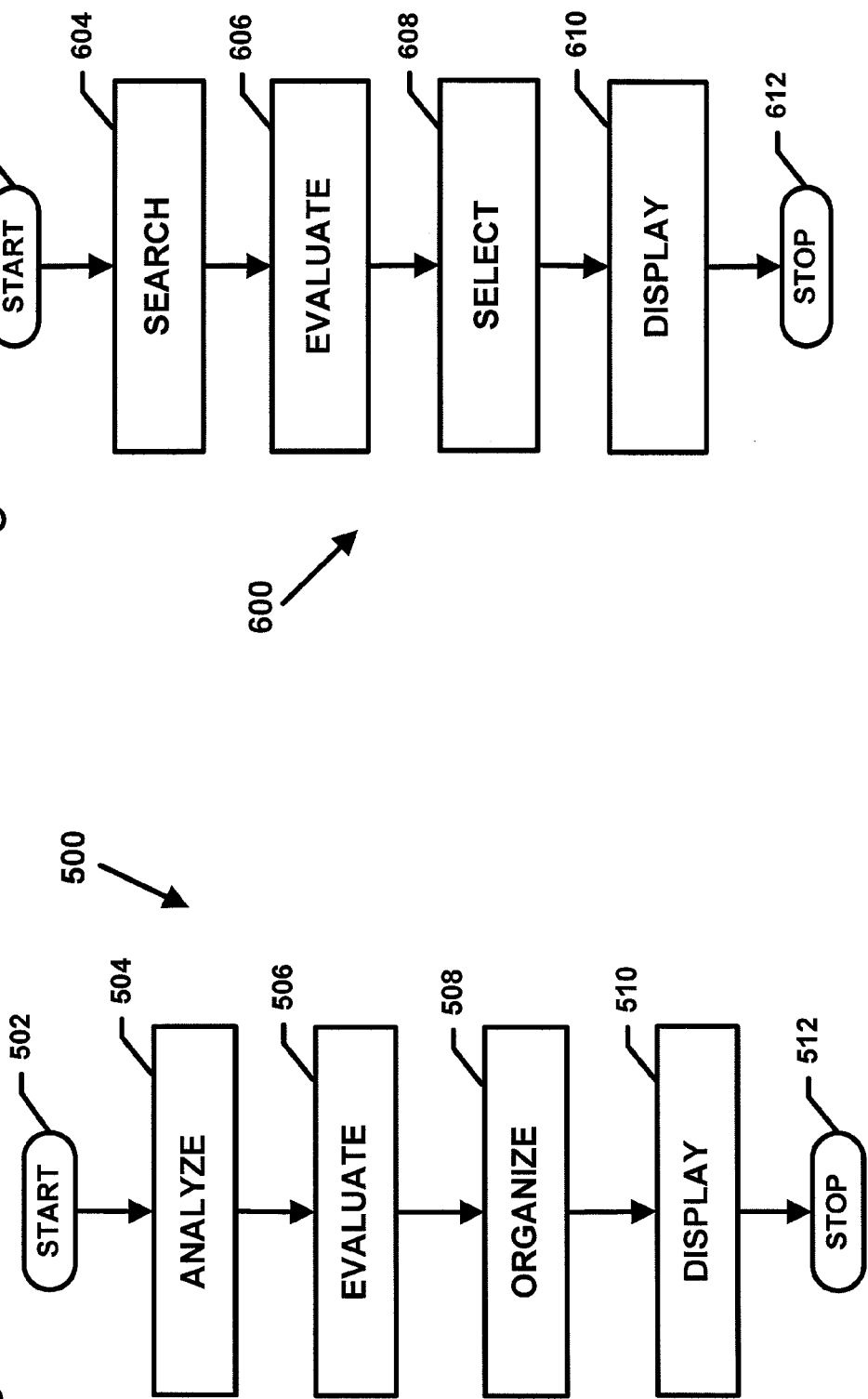
FIG. 5 is a flowchart illustrating an operational flow for a generation process by which a patient report is generated in accordance with the principles of the present invention.

FIG. 5 is a flowchart illustrating an operational flow for a generation process 500 by which patient reports can be generated. In an embodiment, the generation process 500 is implemented by the computing device 250. In another embodiment, the generation process 500 is implemented by the programmer 230. In other embodiments, the generation process 500 can be implemented by any desired computing device configured to be accessed by the clinician and/or the patient.

The generation process 500 initializes and begins at a start module 502 and proceeds to an analyze operation 504. The analyze operation 504 examines the information obtained from the patient database on the computing device 250 to identify treatment events. For example, the analyze operation 504 can search the compiled information for a treatment event indicating the commencement of a therapy session and can identify a timestamp indicating when the treatment event took place.

An evaluate operation 506 can compare the timestamp of the treatment event with the therapy schedule stored on the implementing computing device or stored on the regulator 210 to determine whether the treatment event occurred according to schedule. An organize operation 508 arranges at least some of the identified treatment events and timestamps into a meaningful format to generate a patient report. For example, the organize operation 508 can arrange selected treatment events in chronological order by date and/or time.

A display operation 510 renders the treatment event information for display to the clinician, patient, or other user as one or more reports (e.g., a patient use report, a therapy delivery report, a battery charging report, etc.). For example, the display operation 510 can select particular treatment events (e.g., turning on the controller 220, aligning the controller 220 with the regulator 210, etc.) to display. Examples of patient reports are described in further detail herein. The generation process 500 completes and ends at a stop module 512.

The generated patient reports can be analyzed by the clinician to determine appropriate treatment modifications and/or to provide appropriate patient counseling on using the treatment system 200.

For example, a therapy delivery report can be used by the clinician to evaluate whether the treatment system 200 is functioning correctly. In general, the therapy delivery report indicates when therapy was provided to the patient by the regulator 210, when scheduled therapy was not provided to the patient, and potential reasons the scheduled therapy was not provided. In an embodiment, the therapy delivery report displays dates and times at which treatment events occurred. For example, the therapy delivery report can display a date and time at which the regulator 210 began a therapy episode, a date and time at which the regulator 210 ended a therapy episode, and/or reasons therapy was not initiated or discontinued prematurely. The therapy delivery report also can display events indicating user operational errors.

In an embodiment in which the patient controls the operation of the regulator 210, a patient typically is scheduled to operate the regulator 210 (e.g., turn on and position the controller 220 adjacent the regulator 210) for a predetermined period of time each day. For example, a patient can be scheduled to operate the regulator 210 for a three hour period each day. Alternatively, the patient can be scheduled to recharge the implant battery at a scheduled time each week. A patient use report can indicate to the clinician whether the regulator 210 was operated by the patient each day at the scheduled time or whether the regulator battery was recharged according to schedule. The patient use report also can indicate potential sources of patient error in which the treatment system 200 was used incorrectly or not at all.

A clinician can employ the patient use reports to aid in determining the success of the treatment system 200 and the prescribed treatment regimen. If the desired results are not achieved after using the system 200 for a period of time, then the clinician may determine initially the system 200 is malfunctioning or the prescribed treatment regimen is ineffectual. In response, the clinician may increase the frequency of therapy episodes, increase the duration of each episode, and/or increase the strength of the treatment to improve performance.

However, if the desired results were not obtained because the patient failed to use the system 200 as directed (e.g., the patient did not position the controller 220 properly with respect to the regulator 210, did not charge the controller battery, or did not turn on the controller 220), then time can be lost in modifying the treatment regimen needlessly. Furthermore, modifying the parameters of the treatment regimen to increase frequency, duration, and/or strength of the treatment based on inaccurate information can be dangerous to the patient.

The patient use reports enable the clinician to distinguish more accurately between ineffective treatment parameters and system misuse by the patient, thereby enabling the clinician to respond more appropriately to treatment concerns. If the desired results were not achieved and the patient reports indicate the treatment system 200 was used correctly and according to schedule, then the clinician may elect to modify the treatment specification and/or the therapy schedule.

Alternatively, if the desired results were not achieved and the patient use report indicates patient misuse, e.g., the patient repeatedly failed to turn on the controller 220, then the clinician may elect not to change the treatment parameters. Instead, the clinician can work with the patient to determine why the patient did not operate the system 200 correctly and how to promote correct usage going forward. In other embodiments, the clinician may elect to change the treatment parameters to better suit the patient's lifestyle (e.g., rescheduling therapy episodes to occur at more convenient times).

A battery charge report also can be helpful in aiding the clinician to monitor patient behavior with respect to the treatment system 200. An exemplary battery charge report indicates dates and times during which the controller battery was recharged, charging, or not charged. Based on this information, the clinician can counsel the patient on better habits if the patient has been negligent about charging the controller battery or recharging the regulator battery. Alternatively, the clinician can work with the patient to adjust the therapy schedule to fit better with the patient's lifestyle.

Providing Relevant Default Values

The patient information compiled on the computing device 250 can be processed by the treatment system 200 to provide relevant default treatment parameters to a clinician. For example, the computing device 250 can provide relevant default treatment specification values (e.g., amplitude or frequency of the regulator signal) and/or therapy schedule default values (e.g., duration of therapy episodes, timing of treatment cycles, etc.) to a programmer 230. Alternatively, the computing device 250 can provide the programmer 230 with sufficient patient information to enable the programmer 230 to determine relevant default values for a particular patient.

Providing relevant default values can aid the clinician in selecting actual treatment values. The clinician can utilize the default values as a starting point in establishing appropriate treatment settings and therapy schedules for the patient. Non-limiting examples of the types of default values that can be provided by the treatment system 200 include the type of treatment applied, the duration of each treatment, and the intensity of each treatment.

For example, in the case in which a regulator 210 is electrically coupled to the vagal nerves of a patient to treat obesity, the clinician typically programs the frequency of the signal applied to the nerves, the duration of each signal, and how often the signal is repeated. In the case in which a regulator 210 is electrically coupled to the patient's heart to aid in cardiac rhythm management, the clinician can specify at what point the regulator 210 will apply treatment, the initial dose applied, and the degree to which the dose is increased over time.

Typically, the default values are generated to be relevant to a particular patient. In some embodiments, the default values can be selected based on the track history of the patient. In other embodiments, the default values can be selected based on settings utilized with other patients having similar disorders or biological configurations. For example, the default values can be provided based on a determined success rate correlated to the parameter values used in similar patients.

Figure 6:
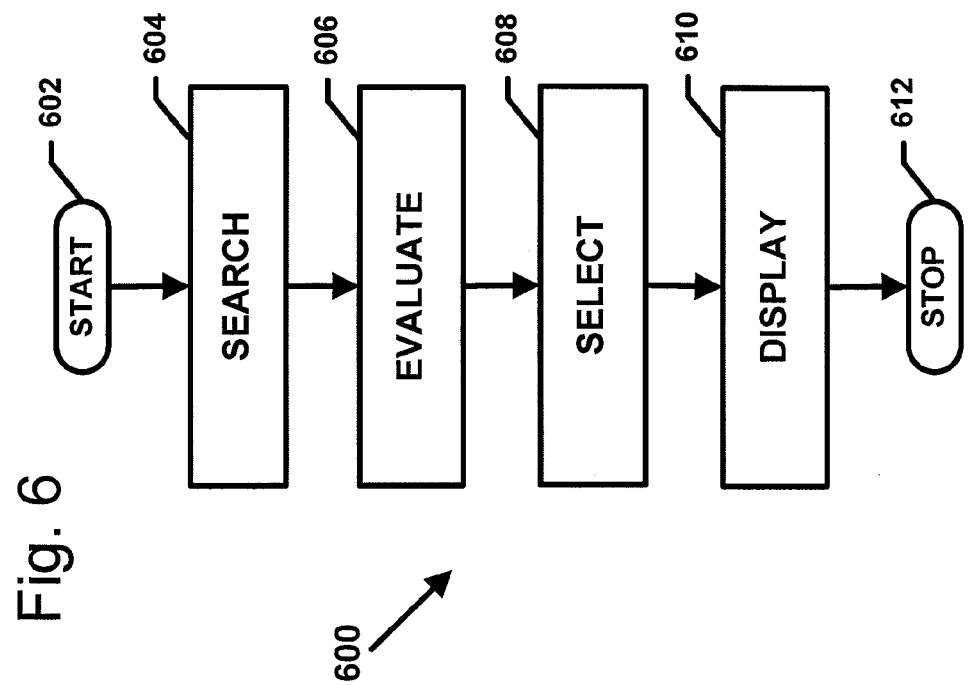
FIG. 6 is a flowchart illustrating an operational flow for a suggestion process by which the computing device or programmer can provide value recommendations for patient treatment in accordance with the principles of the present invention.

FIG. 6 is a flowchart illustrating an operational flow for an exemplary suggestion process 600 by which the computing device 250 or the programmer 230 can provide relevant default values of patient treatment parameters to the treating clinician. The suggestion process 600 initializes and begins at a start module 602 and proceeds to a search operation 604. The search operation 604 queries the patient databases stored on the computing device 250 for treatment specification and/or therapy delivery values utilized with other patients having a biological makeup, disorder, or other characteristic similar to the clinician's patient.

An evaluate operation 606 compiles the search results and compares corresponding treatment success rates. A select operation 608 determines which treatment specification and therapy delivery values tend to correlate with greater success rates in patients similar to the clinician's patient. A display operation 610 presents the selected values to the clinician. For example, the display operation 610 can present treatment specification values to the clinician when the clinician is preparing an initial or modified treatment specification for the patient as discussed in greater detail herein. The suggestion process 600 completes and ends at a stop module 612.

In an embodiment, the programmer 230 can display the default values in a text box of a treatment specification programming interface. In another embodiment, the programmer 230 displays the default values in a drop-down menu or other interface tool used by the clinician to input treatment specification values. In an embodiment, a single default value is displayed to the clinician per parameter. In another embodiment, a range of default values can be provided for a given parameter.

Example Application

Referring to FIGS. 7-13, the present invention can be best understood by walking through an example application in which a clinician initiates a treatment program for a patient and then provides follow-up care for the patient. For the purposes of this example application, the clinician uses a programmer 230 to transfer a treatment specification and a therapy schedule to the DTD 260 for download to the patient's controller 220. The DTD 260 also is utilized to transfer stored treatment events from the controller 220 to the computing device 250. In other embodiments, the DTD 260 transfers data between the programmer 230, the computing device 250, and the regulator 210.

Figure 7:
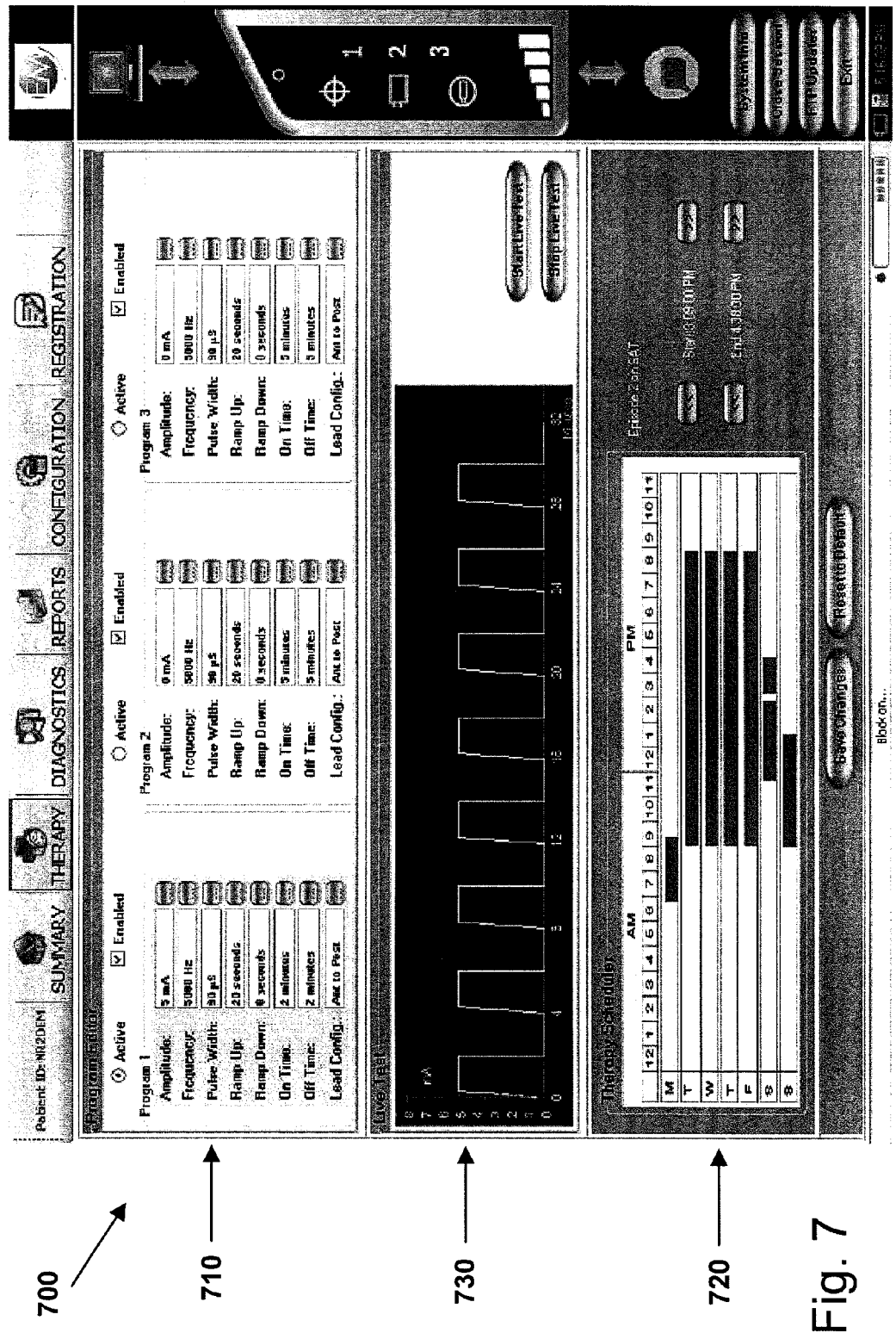
FIG. 7 is an exemplary treatment summary display including a configuration section displaying treatment specification information, a therapy scheduler section displaying a therapy schedule, and an optional live test screen in accordance with the principles of the present invention.

To initiate or modify patient therapy, the clinician views a treatment summary display on the programmer 230 or the computing device 250. The clinician modifies the treatment specification data and/or the therapy schedule data presented to the clinician via the programmer 230. For example, the clinician can view and modify the treatment regimen via the treatment summary display 700 as shown in FIG. 7. The modified data is transmitted from the programmer 230 to the patient's controller 220.

In the example shown, the treatment summary display 700 includes a configuration section 710 displaying treatment specification information, a therapy scheduler section 720 displaying a therapy schedule, and an optional live test screen 730. The clinician can populate the treatment specification 710 by inputting values for one or more treatment attributes. Default values relevant to a particular patient can be provided in the configuration section 710 and the therapy scheduler section 720 as described above. In such embodiments, the clinician can populate the treatment parameter values based, in part, on the default values.

Figure 8:
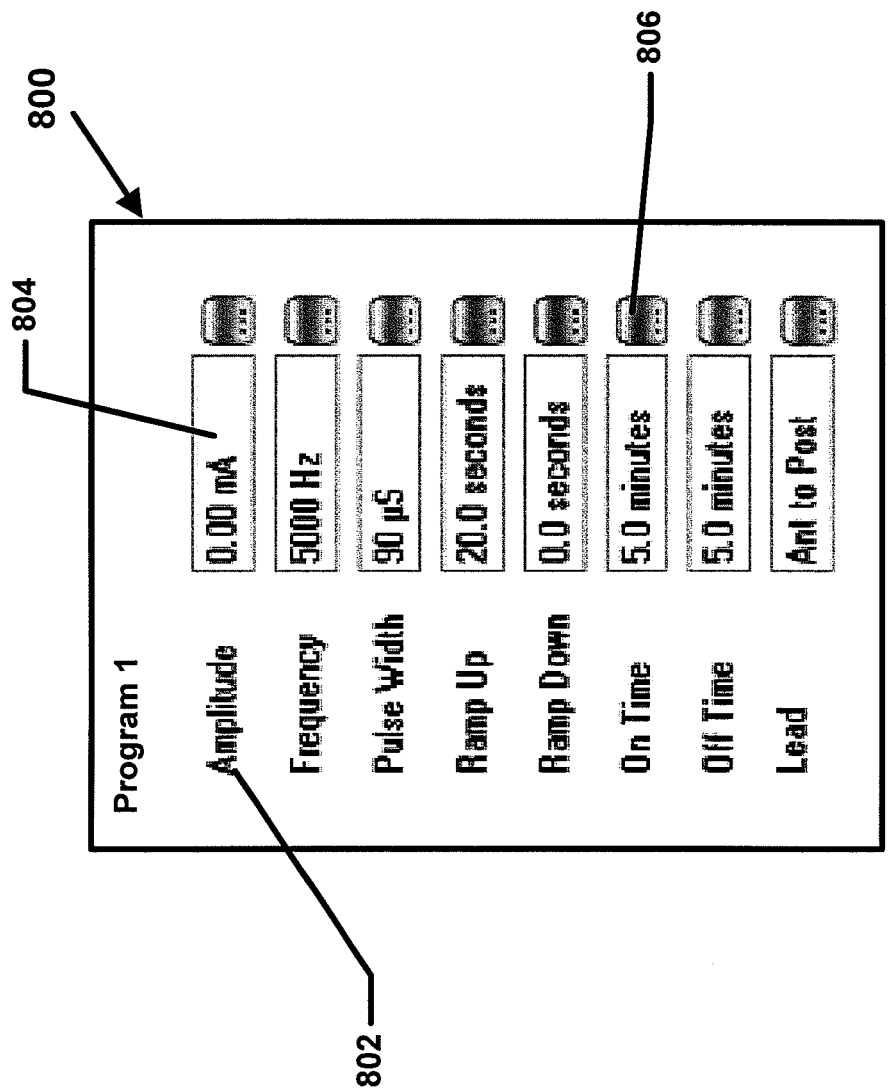
FIG. 8 is an exemplary treatment specification interface having multiple treatment attributes, such as amplitude of the treatment signal, frequency of the treatment signal, and lead configuration, to which a clinician can assign values in accordance with the principles of the present invention.

An example of a treatment specification interface tool is shown at 800 in FIG. 8. The treatment specification includes values 804 associated with treatment attributes 802. In the example shown, treatment attributes 802 include amplitude of the treatment signal, frequency of the treatment signal, and lead configuration (i.e., anterior to posterior or vice versa). The clinician can modify the treatment values 804 by typing information into the text boxes in which the values 804 appear. Alternatively, the clinician can modify the treatment values 804 by selecting from a list of possible values obtained via a menu tool 806.

Figure 9:
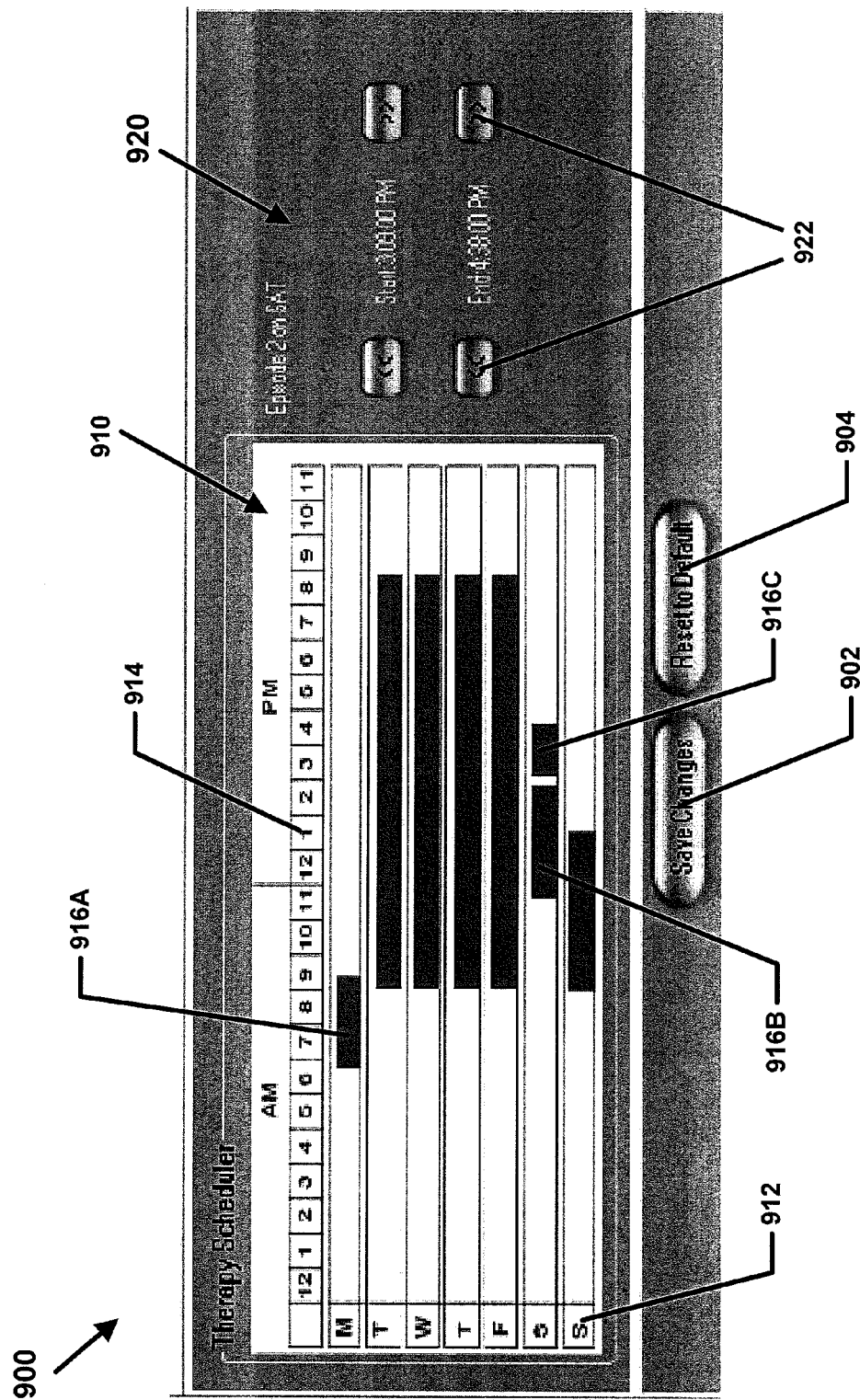
FIG. 9 is an exemplary therapy schedule interface divided into a summary section and a management section in accordance with the principles of the present invention.

The therapy schedule also can be modified by the clinician on the programmer 230. An example of a therapy schedule display is shown at 900 in FIG. 9. The therapy schedule 900 shown in FIG. 9 is divided into a summary section 910 and a management section 920. The summary section 910 is broken out by day (e.g., in rows 912) and by hour (e.g., in columns 914) to indicate at which times of day the therapy episodes should be implemented.

In an embodiment, a therapy episode can be scheduled to begin at a specific time each day. For example, the presence of a solid bar 916A in the treatment summary section 910 indicates a therapy episode should begin at 6:45 am and proceed until 9:15 am on Monday. In other embodiments, therapy episodes can be scheduled to span two or more days (e.g., from late evening one day to early morning the next day).

Alternatively, multiple therapy episodes can be scheduled per day. For example, the solid bar 916B in the treatment summary section 910 indicates a first therapy episode should begin at 11:30 am on Saturday and end at 3:00 pm on Saturday. A second therapy episode (see 916C) is scheduled to begin fifteen minutes later at 3:15 pm on Saturday and to end at 4:45 pm on Saturday.

The treatment summary section 910 can be modified by the clinician to alter the therapy schedule of the patient. In some embodiments, the clinician directly interacts with the graphics displayed in the summary section 910. For example, the clinician can move or stretch existing episode time blocks to extend over different time periods via a mouse or other input tool. In the example shown, the clinician can choose which therapy episode to modify by selecting the corresponding indicia 916 in the summary section 910.

In other embodiments, the clinician can use the treatment management section 920 of the display 900 to modify the therapy schedule. In general, the treatment management section 920 includes user interface tools 922 (e.g., buttons, text boxes, check boxes, radio buttons, etc.) with which the clinician can modify the treatment schedule.

For example, in the embodiment shown in FIG. 9, the management section 920 includes a first set of buttons to increment or decrement the start time of a therapy episode and a second set of buttons to increment or decrement the end time of a therapy episode. In other embodiments, the management section 920 can include additional user interface tools to add, delete, and/or select therapy episodes, to adjust the timing of treatment cycles, and to copy/paste therapy episodes between days.

In an embodiment, the start time and end time of each therapy episode can be incremented or decremented in 15-minute units. In other embodiments, episode time blocks can be defined in shorter or longer increments. In an embodiment, the duration of the "on" time and "off" time of a treatment cycle can be specified in discrete time periods. For example, the duration of each state can be specified in one-minute increments. When the clinician has finished programming the therapy schedule, the settings can be saved by clicking on button 902 or another interface tool. Alternatively, the clinician can restore or load a default therapy schedule via interface tool 904.

The clinician can test the new therapy parameters using a live test option 730 from FIG. 7. The live test feature 730 instructs the regulator 210 to begin a treatment episode immediately for a duration of time. In an embodiment, the duration of the test episode is predetermined by the clinician. In another embodiment, the treatment episode lasts until the clinician sends instructions to stop the episode from the programmer 230 via the DTD 260. Results of the test can be displayed to the clinician substantially in real-time on the programmer 230 via the DTD 260. The clinician can modify the treatment specification and/or the therapy schedule based on the clinician's analysis of the displayed test results.

In general, the test results are transmitted from the regulator 210 to the DTD 260 and then to the programmer 230. In an embodiment, the DTD 260 accesses (i.e., establishes a communicative link with) the programmer 230 to transmit the test results to the clinician. In another embodiment, the programmer 230 accesses the DTD 260 to obtain the test results. In yet another embodiment, the DTD 260 logs the test results on the computing device 250. In such embodiments, the clinician can directly access the computing device 250, access the computing device 250 over a network, or access the computing device 250 via the programmer 230 to obtain the test results.

As discussed above, the clinician can monitor the effects of the treatment regimen on the patient using the therapeutic system 200. For example, the computing device 250 and the DTD 260 can be configured to transfer and store treatment events from the regulator 210 periodically. The clinician can select any convenient time to follow up with the patient or check-in on the patient's progress via the stored treatment events. To aid the clinician in the follow-up analysis, the computing device 250 or the programmer 230 can generate patient reports.

For example, FIG. 10 illustrates an exemplary patient use report 1000 indicating whether the patient correctly used the treatment system 200 over a period of time in accordance with the principles of the present disclosure. In the example shown, the report 1000 includes a table 1020 listing patient usage statistics over a period of time. The range in time over which patient usage is displayed can be selected using interface tools (e.g., drop down menus, text boxes, etc.). In the example shown, start and end dates for a date range can be selected from drop down menus 1002, 1004, respectively.

The patient use table 1020 has a first column 1021 listing dates within the specified range and a second column 1022 listing a percentage value indicating a degree to which the patient utilized the system on the respective date. The table 1020 also includes columns identifying potential reasons the system was not used. In the example shown, the patient use table 1020 includes five additional columns 1023, 1024, 1025, 1026, 1027, each additional column identifying one potential cause of patient non-use.

The first two additional columns 1023 and 1024 identify problems with a transmission unit 223 (FIG. 2) of the controller 220. The first column 1023 contains values indicating what percentage of the scheduled operation time consisted of non-use due to the transmission unit 223 of the controller 230 being disconnected from (or out of contact with) the controller 220. The second of these columns 1024 indicates for each day at what percentage of the scheduled operation time the transmission unit 223 was incorrectly positioned with respect to the implanted regulator 210. For example, according to the patient use table 1020 of FIG. 10, the transmission unit 223 was not properly connected just over 3% of the time on Jan. 21, 2007 and only 0.01% of the time two days prior.

The second two columns 1025 and 1026 identify problems with the patient remembering to charge the battery of the controller 220. Column 1025 contains values indicating what percentage of the scheduled operation time consisted of non-use due to the controller 220 not being powered (e.g., not being charged). Column 1026 contains values indicating how often the patient did not use the system because the system was charging at the specified use time. In other embodiments, a column may indicate problems in recharging the regulator battery. The final column 1027 indicates how often the patient failed to use the system for unknown reasons.

Figure 11:
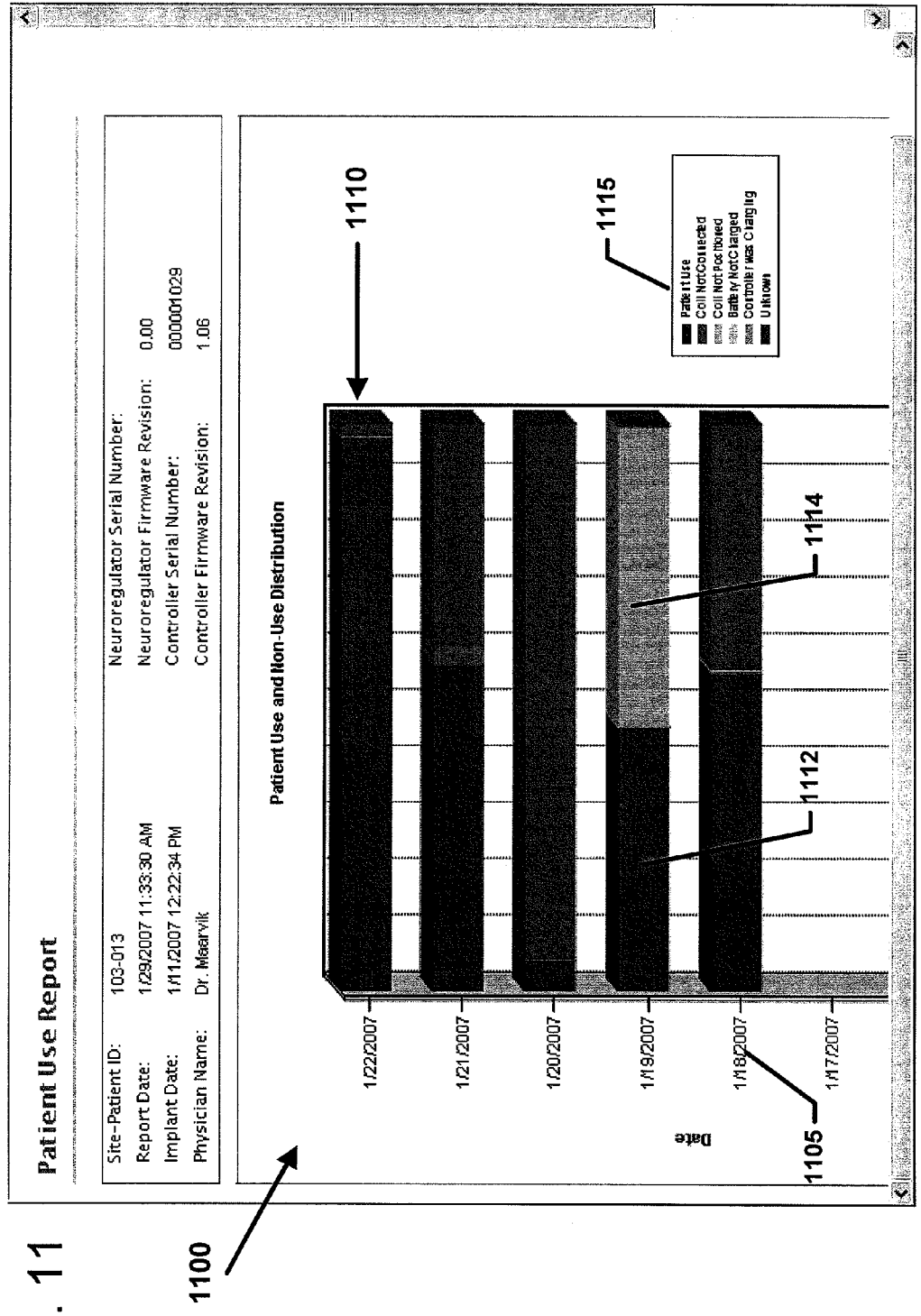
FIG. 11 illustrates an exemplary graph mapping out correct usage of the treatment system and issues experienced over one or more days of scheduled therapy in accordance with the principles of the present disclosure.

As shown in FIG. 11, the patient use report can include a graph 1100 mapping out correct system usage and problems experienced over one or more days. In the example shown, a row 1110 of the graph 1100 represents patient usage for a particular day 1105. Each row 1110 extends from a 0% line to a 100% line. The row is broken into segments to indicate what percentage of each day corresponds with a particular operational status. A key 1115 identifying the segments is provided.

In the example shown, a first segment 1112 shown under Jan. 19, 2007 indicates the system was used correctly for about 45% of the scheduled operating time of Jan. 19, 2007. A second segment 1114 indicates the controller battery was charging for about 55% of the scheduled operating time. Other segments shown indicate the amount of time over which the transmission unit 223 of the controller 220 was not properly connected to the controller 220 or the system 200 was not operating correctly for unknown reasons on a given day.

If desired, a report can be generated for each day within a range of selected dates. FIG. 12 illustrates an example of one such report 1200. In an embodiment, the daily patient usage report 1200 is chosen for display by selecting a row displayed in the patient usage table 1020 of FIG. 10 or a row 1110 in the graph 1100. The report 1200 includes a table 1220 having the same columns as table 1020 of FIG. 10. However, the values in the table indicate how often the patient correctly operated the system throughout a given day. In the example shown, the table 1220 is divided into hourly segments 1221. Allowing the clinician to analyze patient behavior in detail over the course of a day enables the clinician to design more effective therapy schedules to suit the lifestyle of a particular patient.

To determine whether treatment was delivered to a patient as scheduled, the clinician analyzes compiled information including treatment events recorded by the controller 220 (or the regulator 210). The compiled information can be displayed in a therapy delivery report. An example of a therapy delivery report is shown at 1300 in FIG. 13. The therapy delivery report 1300 includes a table 1301 indicating for each day within a range of days whether treatment was delivered during a scheduled delivery time and, if not, why treatment was not delivered.

In the example shown, the first column 1305 in table 1301 lists days on which treatment was scheduled. The second column 1310 indicates for each day in column 1305 what percentage of the scheduled treatment was delivered to the patient in accordance with the therapy schedule. For example, if therapy was delivered to the patient for about half of the scheduled treatment duration, then the second column 1310 would contain an indication of 50%.

The remaining columns (indicated generally at 1350) in the table 1301 indicate potential reasons therapy was not delivered to the patient at the designated times. One subset of possible reasons includes patient error (e.g. forgetting to turn on the system). In the example shown, the columns (indicated generally at 1320) indicating patient error are the same as some of the columns 1023-1026 found in the patient use report 1000 of FIG. 10. In other embodiments, the columns 1320 can indicate the occurrence of other patient errors or other reasons for patient non-use.

Additional potential causes of non-deliverance of treatment are listed in columns 1330, 1332, 1334, 1336, and 1338 of therapy delivery table 1301. Column 1330 indicates when the transmission unit 223 of the controller 220 suffers from an electrical short. Column 1332 indicates when the wrong transmission unit 223 is coupled to the controller 220. Depending on circumstances, this problem source also could fall within patient error. Link errors and system errors are indicated in columns 1336 and 1338, respectively. These errors may indicate a problem with the operation of one or more of the devices 210, 220, 260 of the system 200, rather than with patient usage.

Column 1334 indicates when the impedance of the regulator 210 (i.e., the strength of the electrical signal transmitted between the regulator 210 and the body of the patient) has decreased beyond a predetermined threshold. For example, the regulator 210 can be configured to transmit an electrical signal to first and second leads which are coupled to nerves or muscles of the patient. If one or both of the leads become detached from the nerves, or if a dielectric material builds up between the leads and the nerves, then the impedance of the electrical signal will decrease. If the impedance sufficiently decreases, then the designated amount of therapy will not be delivered to the patient.

Using the above described patient reports, the clinician can gain a clearer understanding of the effectiveness of the treatment system 200. In other embodiments, other types of patient reports can be utilized by the clinician. For example, the clinician can view a battery recharge report (indicating when the controller battery was recharged), a lead status report (indicating the impedance of the electrical signals of the leads), or a therapy history report (indicating prior treatment specifications and/or therapy schedules used with the patient).

Automatic Updating

Figure 14:
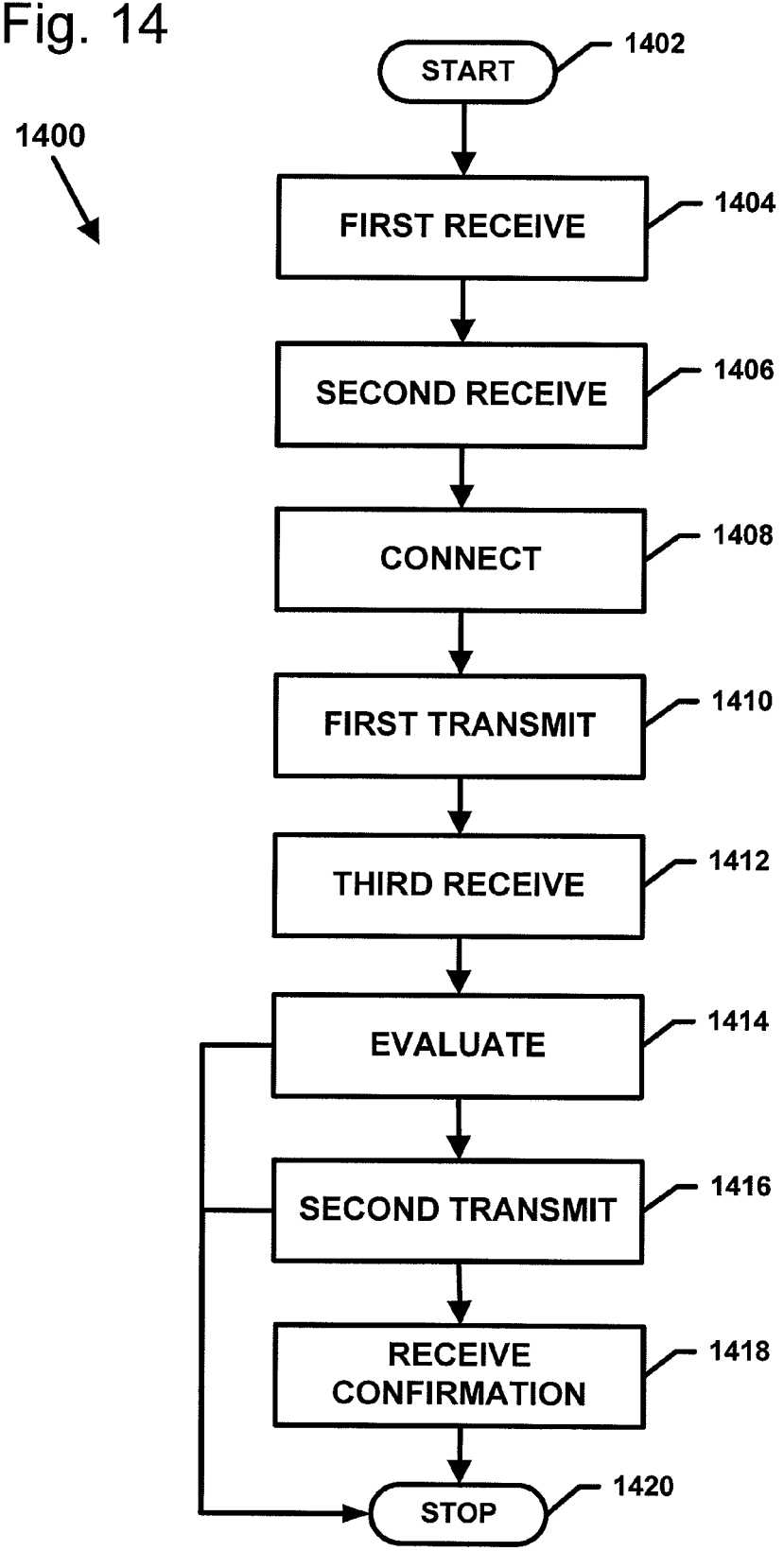
FIG. 14 is a flowchart illustrating an operational flow of an update process by which a remote computing device automatically updates software on therapeutic devices of a therapeutic system in accordance with the principles of the present disclosure.

Referring to FIGS. 14 and 15, the DTD 260 also can be used to provide software updates to the patient's controller 220 and regulator 210. FIG. 14 is a flowchart illustrating an operational flow of a first exemplary update process 1400 by which the computing device 250 initiates a therapeutic software update for one or more patients. Update process 1400 automatically distributes the updated software to the patient devices for installation.

In an embodiment, the computing device 250 updates the software executing on the regulator 210 of each patient. In another embodiment, the computing device 250 updates the software executing on the controller 220 of each patient. In yet another embodiment, the computing device 250 receives software updates for both the regulator 210 and the controller 220 of each patient. In other embodiments, the computing device 250 can receive software updates for any device in therapeutic system 200.

The first update process 1400 initializes and begins at a start module 1402 and proceeds to a first receive operation 1404. The first receive operation 1404 obtains updated software for installation on one or more patient devices 210, 220, 260 of a therapeutic system 200. For example, the first receive operation 1404 can acquire updated software from a software provider when a newer version is released. Alternatively, updated software can be downloaded to the computing device 250 by the clinician.

A second receive operation 1406 receives instructions from a clinician to update the software on one or more devices 210, 220, 260 of therapeutic system 200 with the software obtained in the first receive operation 1404. The instructions can specify a schedule according to which the updates are to be downloaded and/or installed on the therapeutic devices 210, 220, 260. A connect operation 1408 provides a communications link between the computing device 250 and the DTD 260 of each patient scheduled to receive the updated software. Alternatively, the computing device 250 can be programmed to automatically initiate communication with the DTD 260 when relevant updated software is received.

A first transmit operation 1410 provides instructions from the computing device 250 to the DTD 260 to determine what software is installed on the devices 210, 220 of the therapeutic system 200. For example, the first transmit operation 1410 can provide instructions to the DTD 260 to connect to the controller 220 and query the controller 220 regarding the version of the software executing on the controller 220 or the regulator 210. In another embodiment, the first transmit operation 1410 can provide instructions to the DTD 260 to communicate with the regulator 210 to determine which version of software is installed on the regulator 210.

A third receive operation 1412 obtains a response from the DTD 260 regarding what software versions are installed on the devices 210, 220 of the therapeutic system 200. An evaluate operation 1414 compares the software version indicated in the response from the DTD 260 with the software updates stored on the computing device 250. If the evaluate operation 1414 determine the devices 210, 220 of the therapeutic system 200 have the updated software already installed, then the update process 1400 completes and ends at a stop module 1420.

Alternatively, if the evaluate operation 1414 determines that one or more of the devices 210, 220 should be updated, then the update process 1400 proceeds to a transmit operation 1416, which transfers the software updates to the DTD 260 along with instructions to forward the updates to the appropriate therapeutic devices 210, 220 of the therapeutic system 200. An optional confirm operation 1418 can provide confirmation to the computing device 250 from the DTD 260 that the software updates were transmitted to and installed on the appropriate therapeutic devices 210, 220. The first update process 1400 completes and ends at stop module 1420.

In an alternative embodiment, each individual DTD 260 can initiate a determination of whether updated software is available for the devices 210, 220 of the therapeutic system 200. For example, FIG. 15A is a flowchart illustrating an exemplary assessment process 1500A by which the DTD 260 determines the current version of software executing on the therapeutic devices 210, 220 of system 200.

The assessment process 1500A initializes and begins at a start module 1502 and proceeds to a connect operation 1504. The connect operation 1504 provides a communication link between the DTD 260 and the patient's controller 220. As discussed above, the DTD 260 can communicate with the controller 220 via a cable connection or a wireless connection. Alternatively, the connect operation 1504 can provide a communications link between the DTD 260 and the regulator 210.

A query operation 1506 determines the current software versions stored and operating on the controller 220. In an embodiment, the query operation 1506 can determine the current software version operating on the regulator 210. In one such embodiment, the query operation 1506 queries the controller 220, which queries or has queried the regulator 210. In another such embodiment of the query operation 1506, the DTD 260 queries the regulator 210 directly.

A receive operation 1508 obtains a response indicating the software version executing on the controller 220 and/or the software executing on the regulator 210. The assessment process 1500A completes and ends at a stop module 1510. In alternative embodiments, the DTD 260 can determine the software version executing on itself.

Figure 15B:
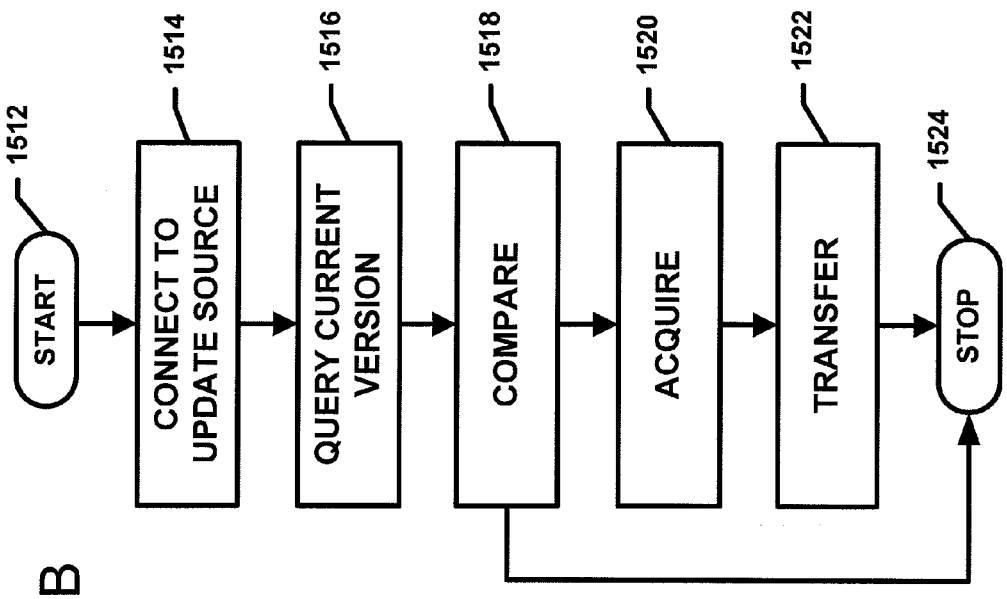
FIG. 15B is a flowchart illustrating an operational flow for an update process by which a DTD checks for updates on a remote computing device in accordance with the principles of the present disclosure.
Figure 15A:
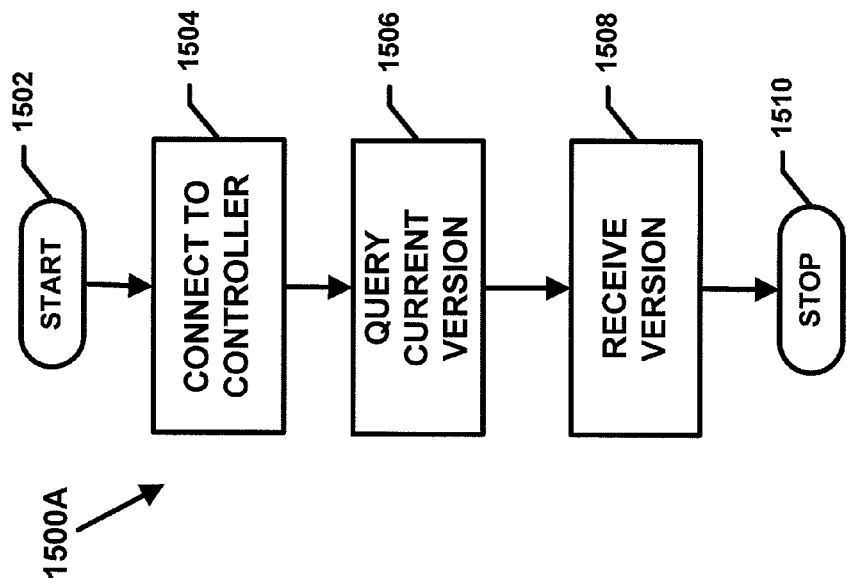
FIG. 15A is a flowchart illustrating an assessment process by which a DTD can determine a current version of software operating on one or more therapeutic devices of a therapeutic system in accordance with the principles of the present disclosure.

FIG. 15B is a flowchart illustrating an update process 1500B by which the DTD 260, the controller 220, and/or the regulator 210 can obtain software updates from an update source, such as the computing device 250. Typically, the update process 1500B is executed by the DTD 260 after execution of the assessment process 1500A discussed above. The update process 1500B initializes and begins at a start module 1512 and proceeds to a connect operation 1514.

The connect operation 1514 provides a communication link between the DTD 260 and a source of software updates. For example, the DTD 260 can communicatively link to the computing device 250, the programmer 230, or another source of software updates. The communication link can be provided over a communications network as described above.

A query operation 1516 searches the software update source, e.g., computing device 250, for recent software updates. The query operation 1516 can search for software configured to operate the DTD 260, software configured to operate the controller 220, and/or software configured to operate the regulator 210. For example, the query operation 1516 can obtain a timestamp indicating the date and time at which the software update was uploaded/stored.

An evaluate operation 1518 compares the software stored on the update source with the software operating on at least one of the DTD 260, the controller 220, and the regulator 210. For example, the evaluate operation 1518 can compare the timestamp associated with the software stored on the update source with a timestamp indicating when the software was installed on a particular device 210, 220, 260.

If the evaluate operation 1518 determines the devices 260, 220, 210 of the system 200 are operating the most recent version of the relevant software, then the update process 1500B completes and ends at a stop module 1524. Alternatively, if the evaluate operation 1518 determines software updates exist for one or more of the devices 260, 220, 210, then the update process 1500B proceeds to an acquire operation 1520.

The acquire operation 1520 transfers the updated software from the software source, e.g., computing system 250, to the DTD 260. The DTD 260 can determine whether the updated software should be installed on the DTD 260 or whether the updated software should be distributed to the controller 220 and/or regulator 210 in a transfer operation 1522. The update process 1500B proceeds to the stop module 1524 as described above. In an embodiment, the DTD 260 automatically implements the assessment process 1500A and the update process 1500B. In other embodiments, however, the DTD 260 implements these processes 1500A, 1500B at the prompting of the patient or the clinician.

In other embodiments, software operating on the programmer 230 can be updated using a similar process. For example, the computing device 250 can connect, either directly or through a network 240, to one or more programmers 230. The computing device 250 can initiate a transfer of updated software to the programmers 230. Alternatively, each programmer 230 can connect to the computing device 250 or other update source to assess whether software updates are available and download the updates as appropriate.

Other Applications

Figure 16:
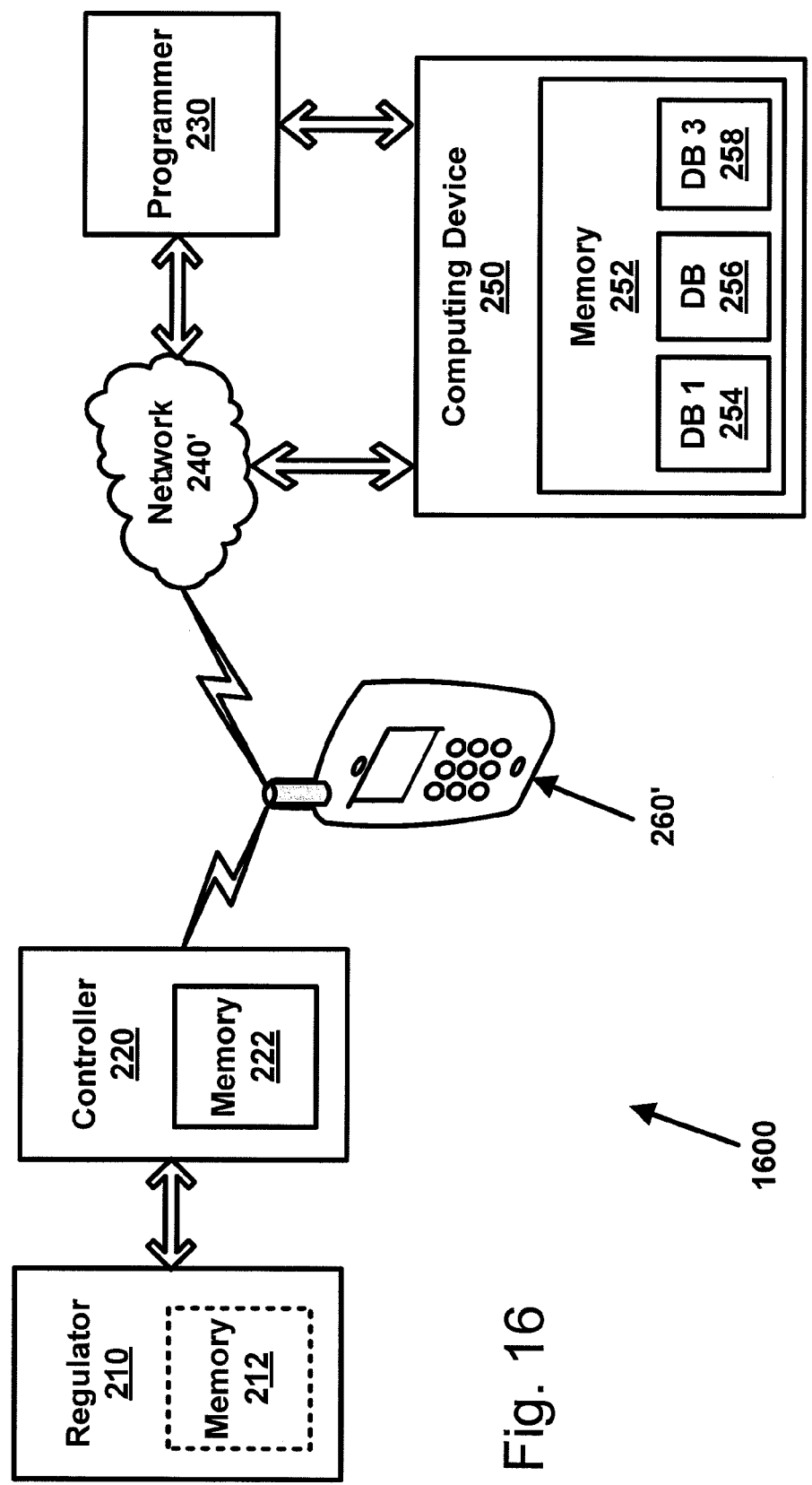
FIG. 16 illustrates an example treatment system in which the DTD is a cellular phone configured to transmit voice data and other data over a network in accordance with the principles of the present disclosure.
Figure 17:
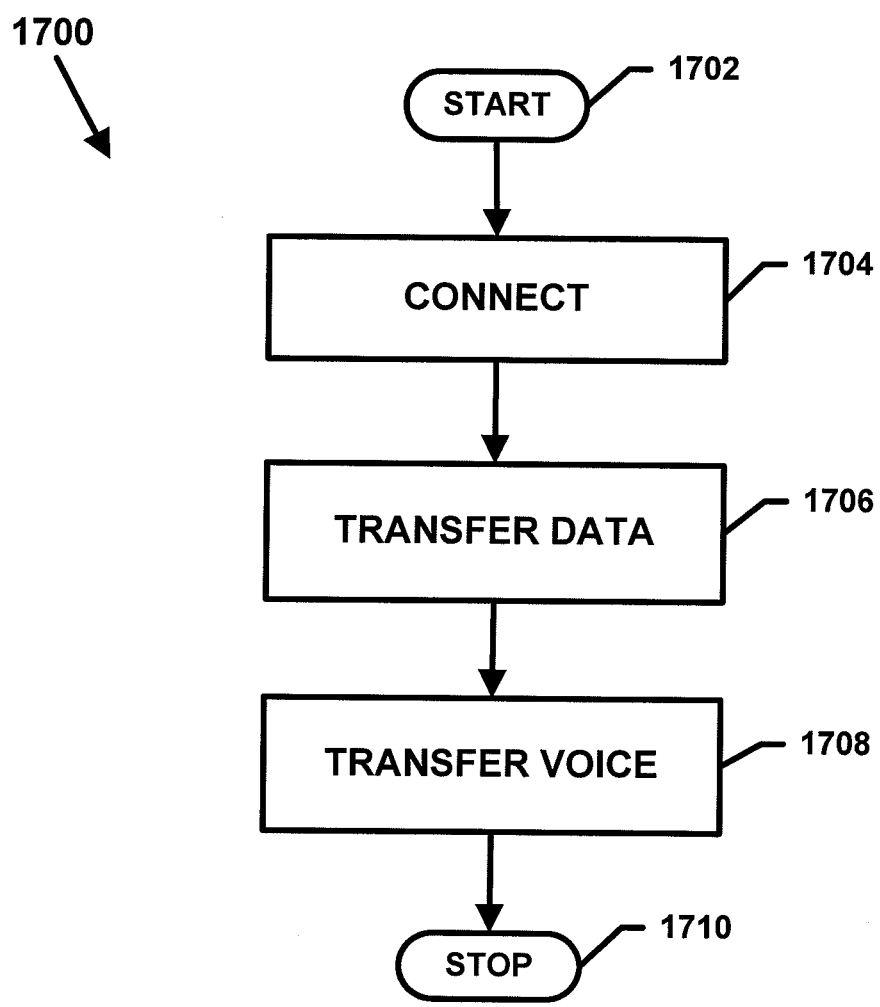
FIG. 17 illustrates an operational flow for an example communication process for enabling a clinician to speak with the patient while transferring treatment information in accordance with the principles of the present disclosure.

Referring now to FIGS. 16 and 17, the DTD 260 is configured to facilitate communication between the clinician and the patient during remote programming and/or testing. For example, the DTD 260 can be a cellular phone 260' or other mobile device configured to transmit data over a cellular network 240' (e.g., a code division multiple access (CDMA) network, a frequency division multiple access (FDMA) network, or another such network). Such a system 1600 is shown in FIG. 16.

The mobile device 260' enables a clinician (e.g., via the programmer 230, the computing device 250, or another remote computing device) to communicate (e.g., upload program information, provide testing instructions, download treatment information, etc.) with a patient's controller 220, even if the patient is located at a remote distance from the clinician. The mobile device 260' also enables the patient to contact the clinician (or vice versa) at substantially any time, regardless of the patient's location (within the limitations of the network 240'). The patient need not be located near a modem or high-frequency wireless local area network (Wi-Fi) connection.

In some embodiments, the mobile device 260' also enables the clinician to transmit and receive voice data to and from the patient. For example, the clinician can transmit oral instructions to the patient via the cellular phone 260' as the clinician is adjusting the patient's treatment or conducting a live test (discussed in greater detail above). The patient can provide immediate feedback to the clinician regarding the patient's physical and mental state as the regulator 210 is being programmed or tested. In other embodiments, the mobile device 260' transmits textual, graphical, and/or executable data between the clinician and the patient.

FIG. 17 illustrates an operational flow for an example communication process 1700 implemented by the cellular phone 260' to enable the clinician to speak with the patient while transferring information to and/or from the controller 220. The example communication process 1700 initializes and begins at a start module 1702 and proceeds to a connect operation 1704. The first connect operation 1704 establishes a communications link between the mobile device 260' and the clinician.

For example, the connect operation 1704 can establish a communications link between the mobile device 260' and the programmer 230 of the clinician. In another embodiment, the connect operation 1704 can establish a communicative link between the mobile device 260' and a remote computing device (e.g., a computing device networked to computing device 250) accessed by the clinician. In other embodiments, the clinician can connect to mobile device 260' via a cellular phone or other mobile device of the clinician. For ease in understanding, the following discussion will assume the clinician communicates with the mobile device 260' via the programmer 230.

A data transfer operation 1706 transmits and receives data between the mobile device 260' and the programmer 230. For example, the first transfer operation 1706 can transfer patient treatment history information from the mobile device 260' to the programmer 230. The data transfer operation 1706 also can transmit a new treatment specification or therapy schedule (discussed in greater detail above) from the programmer 230 to the mobile device 260' for distribution to the patient's controller 220 or regulator 210.

A voice transfer operation 1708 transmits voice data between the mobile device 260' and the programmer 230. Typically, the voice transfer operation 1708 provides two-way voice transmission so the clinician can both speak to and listen to the patient. The communication process 1700 completes and ends at a stop module 1710. In alternative embodiments, the mobile device 260' can transmit and receive other types of communication to and from the programmer 230, such as text and/or graphical data. For example, the mobile device 260' can enable text messaging between the clinician and the patient.

Figure 18:
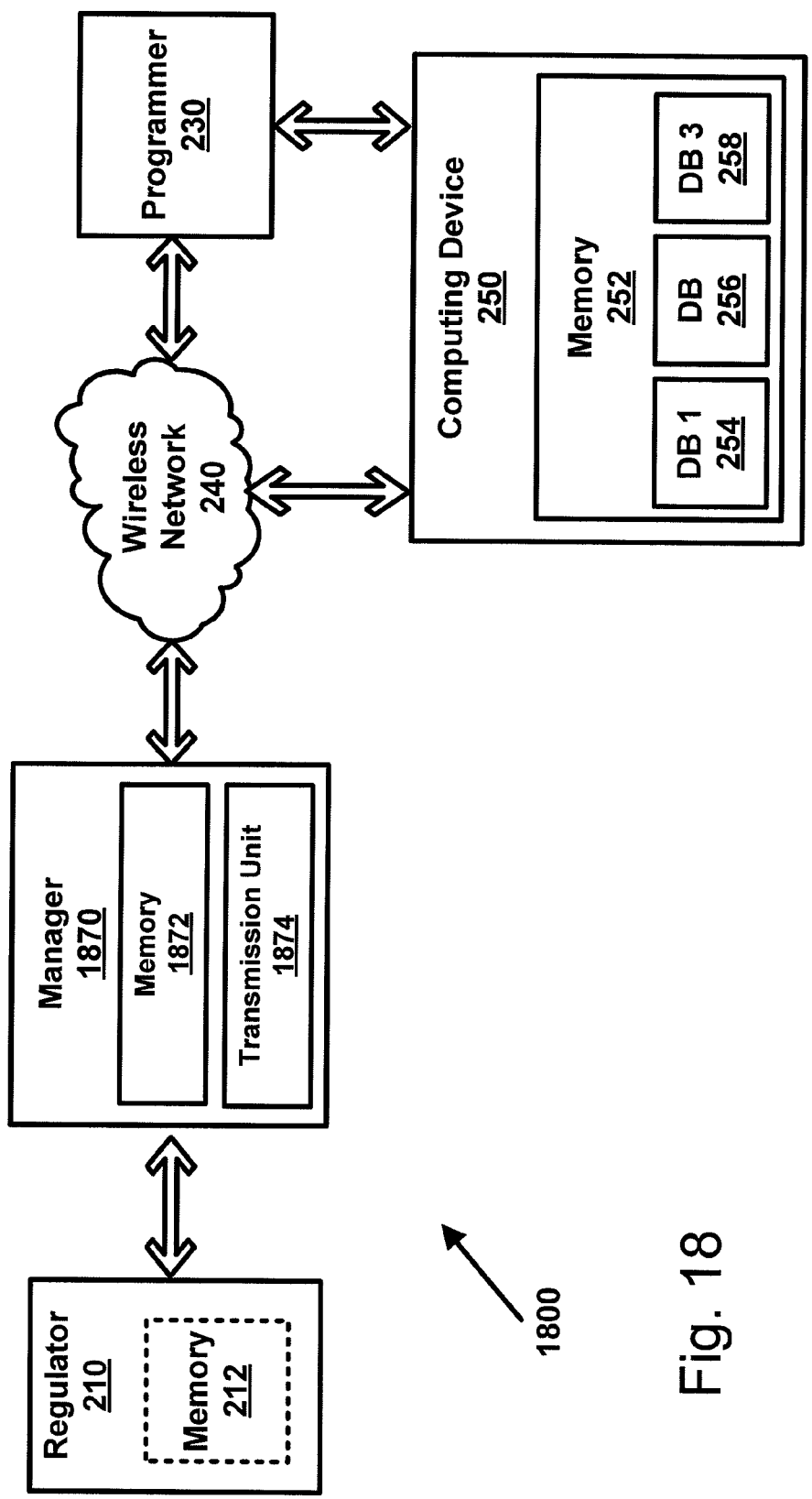
FIG. 18 is an example treatment system in which the controller and the DTD have been combined into a single manager device having a memory and a transmission unit.

FIG. 18 is an example treatment system 1800 in which the controller 220 and the DTD 260 have been combined into a single management device 1870 having a memory 1872 and a transmission unit 1874. In general, the management device 1870 is configured to perform the same functions as the controller 220 and the DTD 260 of treatment system 200. In an embodiment, the management device 1870 also can perform the same functions as mobile device 260' discussed above. Treatment system 1800 facilitates proper usage of the treatment system 1800 by the patient by reducing the number of devices with which the patient must be familiar or that can be lost, damaged, or destroyed.

Any of the above described methods and applications can be implemented using the treatment system 1800. For example, the management device 1870 can control the operation of the implanted regulator 210 by transmitting operation instructions to the regulator 210 using any of the communication means described with respect to controller 220. The management device 1870 also can store treatment events as a treatment history in memory 1872. The management device 1870 can transfer this treatment history to the programmer 230, the computing device 250, or another remote device. The management device 1870 is configured to communicate with the other devices of treatment system 1800 over a wireless communication link from a remote location using any of the communication means described with respect to DTD 260 or 260'.

The above specification, examples and data provide a complete description of the manufacture and use of the invention. Since many embodiments of the invention can be made without departing from the spirit and scope of the invention, the invention resides in the claims hereinafter appended.

We claim:
1. A treatment system comprising:
at least one electrode adapted to be placed on a vagus nerve;
a regulator adapted to be implanted within a patient and connected to the at least one electrode, the regulator configured to apply a treatment to the patient via the electrode, the regulator having a memory configured to store treatment events, at least one therapy parameter, and a therapy schedule;
a computing device remote from the regulator, the computing device comprising a receiver module for receiving treatment events from each patient; a storage module comprising at least one database for storing treatment events from each patient in a database corresponding to each patient, an evaluate module for comparing the treatment events of a first patient with the treatment events of at least one other patient in order to determine which patients are similar to one another to form a subset of patients with similar treatment events, and determining treatment default values corresponding with successful treatment in the subset of patients;
a controller configured to control operation of the regulator and adapted for placement on the patient, the controller including a memory and a transmission coil, the memory of the controller being configured to store treatment events, the transmission coil of the controller being configured to communicate with the regulator and with a data transfer device; wherein the data transfer device communicates with the regulator through the controller;
a data transfer device comprising memory and a transmission unit configured to communicate with the controller and configured to communicate with the computing device over a network to transfer the treatment events from the memory of the controller to the computing device for storage in the patient database and configured to transmit and receive voice data; and
a programmer comprising a)a report module for generating at least one report for each patient based on the treatment events and configured to receive treatment events from the computing device, wherein the at least one report comprises a patient use report indicating whether the patient operated the regulator correctly over a period of time and wherein the programmer is configured to be operated by a clinician at a location remote from the patient, is configured to determine whether the programmer has a current treatment history of the patient; is configured to communicatively couple to the remote computing device to obtain the current treatment history of the patient if the programmer determines the programmer does not have the current treatment history; and is configured to display at least one report generated by the report module;

b) a storage module containing more than one treatment parameter, therapy schedules, and default treatment values corresponding with successful treatment in the subset of patients, c) a user interface configured to display default treatment values corresponding with successful treatment in the subset of patients and to allow selection of a modified treatment value of the treatment parameter and/or therapy schedule from the programmer; and d) a communication module to provide for communication of a modified treatment value to the data transfer device and from the data transfer device to the regulator.

2. The treatment system of claim 1, wherein the programmer is configured to communicatively couple to the data transfer device over a wireless network.

3. The treatment system of claim 1, wherein the programmer is configured to communicate with the data transfer device via a cellular network.

4. The treatment system of claim 1, wherein the at least one therapy parameter is selected from the group consisting of waveform shape, frequency, amplitude, on time, off time, pulse width, ramp up time, ramp down time, lead configuration and combinations thereof.

5. The treatment system of claim 1, wherein the data transfer device is a cellular phone or a tablet computer.

6. A method of operating a treatment system of claim 1 comprising:
    sending a request for treatment events for a patient from the programmer or the computing device;
    receiving a request for treatment events for the patient at the data transfer device;
    sending a request for treatment events for the patient from the data transfer device to the controller of the system of claim 1 in order to obtain treatment events of the patient from the controller;
    receiving treatment events of the patient at the data transfer device from the controller;
    transmitting the obtained treatment events from the data transfer device to the computing device, the obtained treatment events being stored in a patient database at the computing device;
    processing the obtained treatment events on the computing device;
    downloading the patient database from the computing device to the programmer;
    sending default treatment values corresponding with successful treatment in a subset of patients from the computing device to the programmer;
    generating at least one patient report based on the obtained treatment events, wherein generating at least one patient report comprises generating a patient use report indicating whether the patient operated the regulator correctly over a select period of time and default treatment values corresponding with successful treatment in the subset of patients from the computing device to the programmer;
    communicating the at least one patient report to the programmer; and
    displaying the patient report on the programmer.

7. The method of claim 6, further comprising communicating instructions to the patient regarding treatment modifications via voice communication.

8. A method of programming a treatment system of claim 1 comprising:
    selecting one or more treatment parameters and/or a therapy schedule that corresponds to the default treatment values corresponding with successful treatment in the subset of patients;
    transmitting one or more selected treatment parameters and/or a therapy schedule to the data transfer device from the programmer or the remote computing device, wherein the treatment parameters comprise waveform shape, frequency, amplitude, pulse width, on time, off time, ramp up time, ramp down time, lead configuration and combinations thereof;
    transmitting the one or more selected treatment parameters and/or therapy schedule to the controller from the data transfer device;
    transmitting the one or more selected treatment parameters and/or the therapy schedule from the controller to the regulator for storage on the regulator and implementation of the therapy;
    storing treatment events and/or battery status on the regulator implanted in the patient; and
    obtaining the stored treatment event and/or battery status from the implanted regulator and transmitting the stored treatment event and/or battery status to the at least one database associated with the patient in the remote computing device.

9. The method of claim 8, further comprising:
    generating a report of treatment events and/or battery status and displaying the report on the programmer;
    evaluating the report to determine if the therapy is being delivered effectively and/or whether the device is functioning properly;
    modifying the treatment value of at least one treatment parameter and/or therapy schedule to change the amount of therapy delivered if the therapy is not being delivered effectively; and
    transmitting the modified treatment value of the at least one treatment parameter and/or therapy schedule from the programmer to the data transfer device and from the data transfer device to the regulator.

10. The method of claim 9, wherein the report comprises a therapy delivery report indicating whether treatment was provided to the patient at scheduled time intervals over a select period of time.

11. The method of claim 9, wherein the treatment parameters are selected from the group consisting of waveform shape, the amplitude of regulator signal, frequency of the regulator signal, pulse width, ramp up time, ramp down time, on time, off time, lead configuration and combinations thereof.

12. The method of claim 9, wherein the treatment parameters comprise duration of therapy cycles, timing of treatment cycles, and combinations thereof.

13. The method of claim 9, wherein the at least one parameter is modified to a treatment value corresponding with successful treatment in the subset of patients.

* * * * *